United States Patent
Osby et al.

(10) Patent No.: US 11,643,608 B2
(45) Date of Patent: May 9, 2023

(54) PROCESS FOR $C_{5+}$ HYDROCARBON CONVERSION

(71) Applicant: ExxonMobil Chemical Patents Inc., Baytown, TX (US)

(72) Inventors: Terrance C. Osby, Spring, TX (US); Thomas E. Hewitt, III, Conroe, TX (US); Joseph S. Famolaro, Spring, TX (US); Nikki L. Griggs, Houston, TX (US); Ronald J. Cimini, Montgomery, TX (US); Steven M. Slack, Humble, TX (US); Jackie S. Thompson, Spring, TX (US); John R. DeLaney, The Woodlands, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 42 days.

(21) Appl. No.: 17/284,598

(22) PCT Filed: Nov. 4, 2019

(86) PCT No.: PCT/US2019/059698
§ 371 (c)(1),
(2) Date: Apr. 12, 2021

(87) PCT Pub. No.: WO2020/096979
PCT Pub. Date: May 14, 2020

(65) Prior Publication Data
US 2021/0253961 A1     Aug. 19, 2021

Related U.S. Application Data

(60) Provisional application No. 62/756,924, filed on Nov. 7, 2018.

(30) Foreign Application Priority Data

Jan. 21, 2019 (EP) .................... 19152835

(51) Int. Cl.
*C10G 69/06* (2006.01)
*C07C 4/04* (2006.01)
(Continued)

(52) U.S. Cl.
CPC ............... *C10G 69/06* (2013.01); *B01D 3/10* (2013.01); *B01D 3/143* (2013.01); *B01D 3/40* (2013.01);
(Continued)

(58) Field of Classification Search
None
See application file for complete search history.

(56) References Cited

U.S. PATENT DOCUMENTS 2,904,502 A * 9/1959 Shapleigh ................ C10G 9/14
585/650
3,360,946 A   1/1968 Di Napoli
(Continued)

FOREIGN PATENT DOCUMENTS

WO     2018/094336     5/2018

OTHER PUBLICATIONS

U.S. Appl. No. 17/282,418, filed Apr. 2, 2021 Entitled "Process for C5+ Hydrocarbon Conversion" Delaney et al.
(Continued)

*Primary Examiner* — Tam M Nguyen

(57) ABSTRACT

The invention relates to $C_{5+}$ hydrocarbon conversion. More particularly, the invention relates to separating a vapor phase product and a liquid phase product from a heated mixture that includes steam and $C_{5+}$ hydrocarbons, catalytically cracking the liquid phase product and steam cracking the vapor phase product.

20 Claims, 5 Drawing Sheets

(51) Int. Cl.
  *B01D 3/40* (2006.01)
  *B01D 3/10* (2006.01)
  *B01D 3/14* (2006.01)
  *B01J 19/24* (2006.01)
  *C07C 4/06* (2006.01)
  *C07C 7/10* (2006.01)

(52) U.S. Cl.
  CPC ............... *B01J 19/245* (2013.01); *C07C 4/04* (2013.01); *C07C 4/06* (2013.01); *C07C 7/10* (2013.01); *B01J 2219/0004* (2013.01); *C10G 2300/301* (2013.01); *C10G 2300/308* (2013.01); *C10G 2300/4006* (2013.01); *C10G 2300/4012* (2013.01); *C10G 2300/4018* (2013.01); *C10G 2400/30* (2013.01)

(56) References Cited

U.S. PATENT DOCUMENTS

| | | | | |
|---|---|---|---|---|
| 7,404,889 | B1 * | 7/2008 | Powers | C10G 9/14 208/53 |
| 7,714,180 | B2 | 5/2010 | Duhon et al. | |
| 7,993,435 | B2 * | 8/2011 | Stell | C10G 9/00 208/368 |
| 8,877,985 | B2 | 11/2014 | Powell | |
| 9,637,694 | B2 * | 5/2017 | Evans | C10G 69/06 |
| 9,777,227 | B2 * | 10/2017 | Soultanidis | C10G 49/22 |
| 2006/0094918 | A1 * | 5/2006 | McCoy | C07C 4/04 585/650 |
| 2007/0055087 | A1 * | 3/2007 | Powers | C10G 9/36 585/648 |
| 2009/0012340 | A1 * | 1/2009 | Choi | C10G 11/04 585/653 |
| 2009/0050523 | A1 * | 2/2009 | Halsey | C10G 9/00 208/68 |
| 2011/0005970 | A1 * | 1/2011 | Ou | C10G 51/04 208/44 |
| 2012/0168348 | A1 * | 7/2012 | Coleman | C10G 69/00 208/80 |
| 2013/0248419 | A1 * | 9/2013 | Abba | C10G 69/00 208/67 |
| 2014/0357923 | A1 * | 12/2014 | Pavia | B01D 3/16 202/158 |
| 2017/0022429 | A1 * | 1/2017 | Van Willigenburg | C07C 5/327 |
| 2018/0057758 | A1 | 3/2018 | Al-Ghamdi et al. | |
| 2018/0057759 | A1 | 3/2018 | Kandel et al. | |
| 2018/0155638 | A1 * | 6/2018 | Al-Ghamdi | C10G 7/06 |
| 2018/0305273 | A1 * | 10/2018 | Patel | C07C 2/84 |
| 2019/0023999 | A1 * | 1/2019 | Sundaram | C10G 9/36 |
| 2019/0169510 | A1 * | 6/2019 | Pavia | C10G 9/26 |
| 2019/0284485 | A1 * | 9/2019 | Van Willigenburg | B01D 3/38 |
| 2020/0308497 | A1 * | 10/2020 | Harandi | B01D 3/143 |
| 2020/0369966 | A1 * | 11/2020 | Bitting | C10G 9/20 |
| 2021/0130711 | A1 * | 5/2021 | Sundararaman | B01J 19/245 |
| 2021/0246389 | A1 * | 8/2021 | Koseoglu | C10G 69/14 |
| 2021/0388275 | A1 * | 12/2021 | DeLaney | B01J 19/245 |
| 2022/0081380 | A1 * | 3/2022 | Chinta | C10G 2/32 |
| 2022/0204866 | A1 * | 6/2022 | Monson | C10G 51/023 |

OTHER PUBLICATIONS

U.S. Appl. No. 17/281,744, filed Mar. 31, 2021 Entitled "Process for C5+ Hydrocarbon Conversion" Delaney et al.

U.S. Appl. No. 17/282,993, filed Apr. 5, 2021 Entitled "Process for C5+ Hydrocarbon Conversion" Delaney et al.

* cited by examiner

PROCESS FOR $C_{5+}$ HYDROCARBON CONVERSION

CROSS-REFERENCE TO RELATED APPLICATIONS

This application is a US national phase application of PCT Application Serial No. PCT/US2019/059698 having a filing date of Nov. 4, 2019, which claims priority to and the benefit of U.S. Provisional Application No. 62/756,924 having a filing date of Nov. 7, 2018 and European Patent Application No. 19152835.5 having a filing date of Jan. 21, 2019, the disclosures of all of which are incorporated herein by reference in their entireties.

FIELD

The invention relates to $C_{5+}$ hydrocarbon conversion. More particularly, the invention relates to separating a vapor phase product and a liquid phase product from a heated mixture that includes steam and $C_{5+}$ hydrocarbons, catalytically cracking the liquid phase product and steam cracking the vapor phase product.

BACKGROUND

Pyrolysis processes, e.g., steam cracking, convert saturated hydrocarbons to higher-value products, e.g., light olefins such as ethylene and propylene. A mixture of crude oil and water/steam can be heated in a convection section of a steam cracking furnace to produce a heated mixture that can be separated into a vapor phase and a liquid phase. The vapor phase can be steam cracked in the steam cracker furnace, typically in the radiant section, to produce a steam cracker effluent from which various products, such as process gas, steam cracker naphtha (SCN), steam cracker gas oil (SCGO), steam cracker tar (SCT), etc., can be separated. The liquid phase can be catalytically cracked in a fluidized catalytic cracker to produce a catalytically cracked effluent from which various products, such as a $C_4$-overhead, naphtha, a distillate, and a bottoms product, can be separated. Once approach to carrying out such a process is disclosed in U.S. Patent Application Publication No. 2018-0057758.

The bottoms product, which typically includes high boiling hydrocarbons, e.g., a 340° C.+ fraction, is the least valuable product recovered from the a catalytically cracked effluent. Converting the bottoms product into more valuable products typically requires excessive hydrogen addition, expensive separation equipment, and/or the importation of a more valuable hydrocarbon for use as a solvent or diluent that is mixed with the bottoms product to improve the processability thereof.

There is a need, therefore, for improved processes and systems for processing a bottoms product separated from a catalytically cracked effluent.

SUMMARY

Processes and systems for $C_{5+}$ hydrocarbon conversion are provided. Certain aspects of the invention relate to heating a hydrocarbon feed and combining the hydrocarbon feed with an aqueous fluid to produce a heated mixture comprising hydrocarbon and steam, wherein the heating is carried out before, during, and/or after the hydrocarbon feed is combined with the aqueous fluid. These and other aspects also include separating from the heated mixture a vapor phase product and a liquid phase product, catalytically cracking at least a portion of the liquid phase product in the presence of a fluidized catalyst to produce a catalytically cracked effluent, and separating a light hydrocarbon product from the catalytically cracked effluent, wherein the light hydrocarbon product comprises a first $C_2$ hydrocarbon. These aspects also include steam cracking at least a portion of the vapor phase product to produce a steam cracker effluent, and separating from the steam cracker effluent a tar product and an upgraded steam cracker effluent, wherein the upgraded steam cracker effluent comprises a second $C_2$ hydrocarbon; hydroprocessing at least a portion of the tar product to produce a hydroprocessed product; and combining at least a portion of the first $C_2$ hydrocarbon and at least a portion of the second $C_2$ hydrocarbon, and recovering at least a portion of the combined $C_2$ hydrocarbon.

Other aspects of the invention include separating a light hydrocarbon product from the catalytically cracked effluent, wherein the light hydrocarbon product comprises methane, a first $C_2$ hydrocarbon, a first $C_3$ hydrocarbon, and a first $C_4$ hydrocarbon; and separating from the light hydrocarbon product at least a portion of the first $C_4$ hydrocarbon to produce and upgraded light hydrocarbon product. These and other aspects also include demethanizing at least a portion of the upgraded light hydrocarbon product by at least contacting that portion of the upgraded light hydrocarbon product with a first portion of the first $C_4$ hydrocarbon, and recovering (i) a raffinate comprising methane and (ii) an extract comprising $C_2$, $C_3$, and $C_4$ hydrocarbon; and steam cracking the vapor phase product to produce a steam cracker effluent. A tar product and an upgraded steam cracker effluent can be separated from the steam cracker effluent, wherein the upgraded steam cracker effluent comprises a second $C_2$ hydrocarbon, a second $C_3$ hydrocarbon, and a second $C_4$ hydrocarbon, wherein the second $C_4$ hydrocarbon is richer in butadiene in comparison with the first $C_4$ hydrocarbon. At least a portion of the tar product can be hydroprocessed to produce a hydroprocessed product. Butadiene can be removed from the second $C_4$ hydrocarbon to produce an upgraded $C_4$ hydrocarbon. At least a portion of the extracted $C_4$ hydrocarbon can be combined with at least a portion of the upgraded $C_4$ hydrocarbon.

Certain unsaturated products and co-products are within the scope of the invention, as are apparatus for carrying out any of the foregoing processes.

BRIEF DESCRIPTION OF THE DRAWINGS

The drawings described herein are for illustrative purposes only of selected embodiments and not all possible implementations, and are not intended to limit the scope of the present disclosure. Corresponding reference numerals indicate corresponding parts throughout the drawings.

Figure 1:
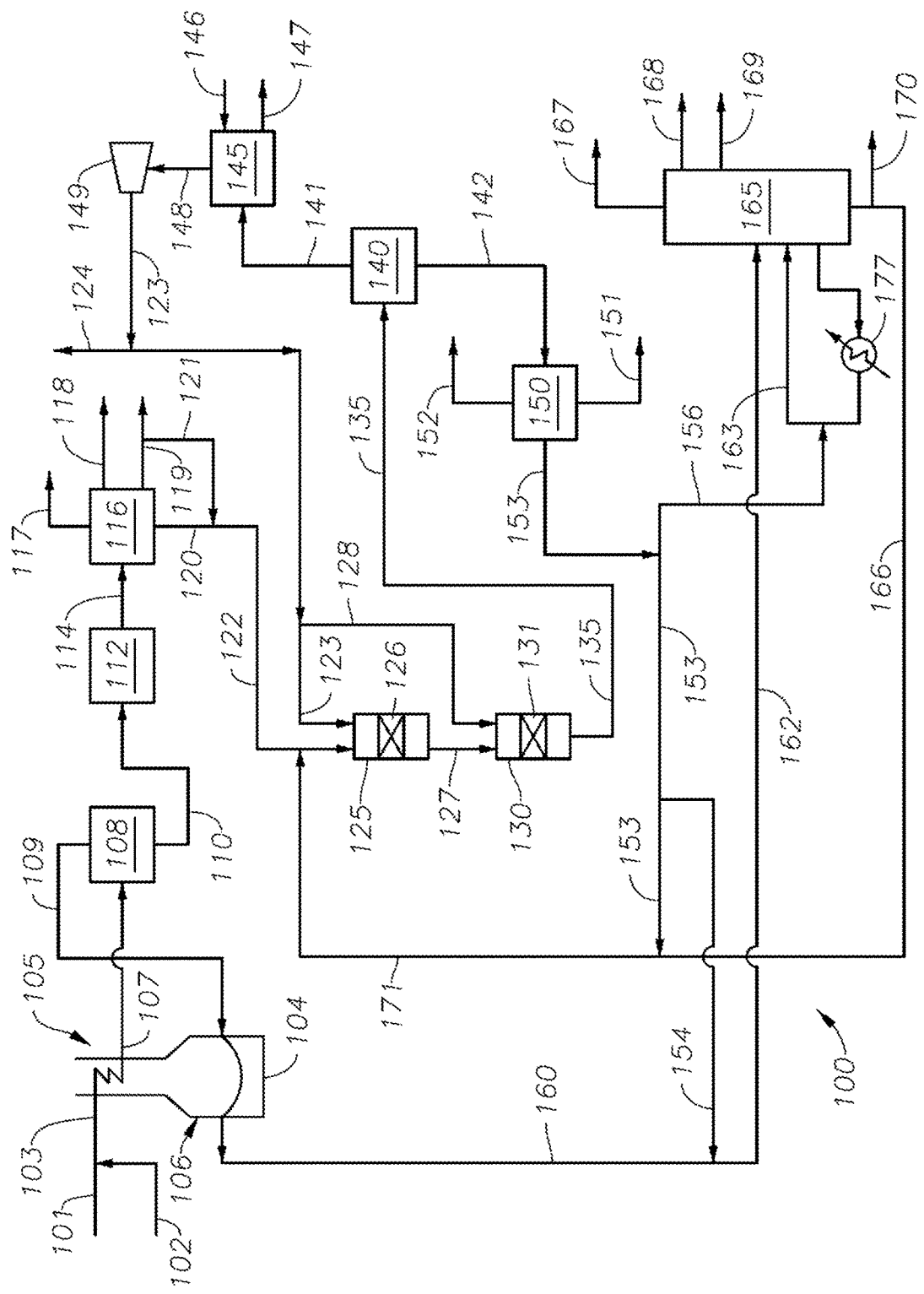
FIG. 1 depicts a schematic of an illustrative system for steam cracking a vapor phase product, catalytically cracking a liquid phase product, and hydroprocessing a bottoms product separated from the catalytically cracked effluent to produce a hydroprocessed product, according to one or more embodiments described.

In each of FIGS. 1-6, features having the same or similar functionality have the same index number.

DETAILED DESCRIPTION

It is to be understood that the following disclosure describes several exemplary embodiments for implementing different features, structures, or functions of the invention. Exemplary embodiments of components, arrangements, and configurations are described below to simplify the present disclosure; however, these exemplary embodiments are provided merely as examples and are not intended to limit the scope of the invention. Additionally, the present disclosure may repeat reference numerals and/or letters in the various exemplary embodiments and across the Figures provided herein. This repetition is for the purpose of simplicity and clarity and does not in itself dictate a relationship between the various exemplary embodiments and/or configurations discussed in the Figures. Moreover, the exemplary embodiments presented below can be combined in any combination of ways, i.e., any element from one exemplary embodiment can be used in any other exemplary embodiment, without departing from the scope of the disclosure.

In some examples, a feed comprising one or more hydrocarbons, e.g., a feed containing $C_{5+}$ hydrocarbons, can be (i) mixed, blended, combined, or otherwise contacted with a diluent (typically an aqueous diluent such as water and/or steam) and (ii) heated to produce a heated mixture, where (i) and (ii) can be carried out a plurality of times and in any order to produce the heated mixture. A vapor phase product or "first" vapor phase product and a liquid phase product or "first" liquid phase product can be separated from the heated mixture. The first liquid phase product can be catalytically cracked in the presence of a fluidized catalyst to produce a catalytically cracked effluent. A bottoms product separated from the catalytically cracked effluent can be hydroprocessed to produce a hydroprocessed product. The first vapor phase product can be steam cracked to produce a steam cracker effluent. A tar product and an upgraded steam cracker effluent that can include, but is not limited to, ethylene and propylene can be separated from the steam cracker effluent. The tar product can be hydroprocessed with the bottoms product.

It has been surprisingly and unexpectedly discovered that the bottoms product and tar product can be hydroprocessed together to produce a hydroprocessed product from which a utility fluid having a certain set of properties and a hydroprocessor heavy product can be separated. All or portions of the utility fluid may find use in various aspects of the invention, e.g., for combining with the tar product, e.g., a tar product flux and/or hydroprocessing aid; as a quench fluid; as a component of the fluxed bottoms, etc. The hydroprocessing can be carried out in stages, e.g., in a pre-treater stage followed by a bottoms product hydroprocessor. In some examples, the hydroprocessor heavy product can be further processed, e.g., by additional hydroprocessing (re-treatment hydroprocessing), to produce a low-sulfur fuel oil boiling-range product that is suitable for use as a fuel oil (a first fuel oil) or a blending constituent thereof.

In other examples, the one or more hydrocarbons can be mixed, blended, combined, or otherwise contacted with water, steam, or a mixture thereof and heated to produce the heated mixture. The first vapor phase product and the first liquid phase product can be separated from the heated mixture. The liquid phase product can be catalytically cracked in the presence of the fluidized catalyst to produce the catalytically cracked effluent. The bottoms product and a cycle oil can be separated from the catalytically cracked effluent. The bottoms product can be mixed, blended, combined, or otherwise contacted with the cycle oil to produce a fluxed bottoms that can be hydroprocessed to produce a hydroprocessed product. In some examples, the fluxed bottoms can include about 5 wt. %, about 10 wt. %, about 15 wt. %, about 20 wt. %, or about 30 wt. % to about 50 wt. %, about 60 wt %, about 70 wt %, about 80 wt %, about 85 wt %, about 90 wt %, or about 95 wt % of the cycle oil, based on a combined weight of the cycle oil and the bottoms product. The tar product (and/or a mixture of the tar product and the utility fluid) can be contacted with the bottoms product before, during, and/or after the bottoms product is contacted with the cycle oil. For example, the fluxed mixture can further comprise the tar product and the utility fluid.

The fluxed bottoms can be hydroprocessed to produce a hydroprocessed product from which the utility fluid product and the hydroprocessor heavy product can be separated. The vapor phase product can be steam cracked to produce the steam cracker effluent. The tar product and the process gas that can include, but is not limited to, ethylene and propylene can be separated from the steam cracker effluent.

It is surprisingly and unexpectedly discovered that the cycle oil can be used as a suitable medium to flux the bottoms to achieve a relatively long run length during hydroprocessing without excessive pressure drop across the hydroprocessing reactor. Although the cycle oil and bottoms product are both components of the catalytically cracked effluent, it was expected that at least a portion of the effluent's naphtha component would be needed to solubilize the bottoms product in the cycle oil. This has been found to not be the case. It has also been discovered that a utility fluid product having a certain set of desirable properties and a hydroprocessor heavy product can be separated from the hydroprocessed product. Prior to combining the cycle oil with the bottoms product it was not expected that the cycle oil would be a suitable medium for fluxing the bottoms product during hydroprocessing under conditions similar to those which had been found to be useful for hydroprocessing steam cracker tar. The catalytic cracking process used to make the cycle oil and the bottoms product are very different from the processes used to make steam cracker tar and the diluents needed for steam cracker tar hydroprocessing. Since these processes are so different, it was expected that the streams derived from the processes would also be quite different, leading to the conclusion that processes similar to those used for hydroprocessing pyrolysis tar would not be usable for processing a bottoms product proceed by catalytic cracking. It is surprisingly found that this is not the case.

It is also surprisingly and unexpectedly discovered that directly contacting the steam cracker effluent with a quench fluid that can be or include the utility fluid product or "first portion" of the utility fluid product can decrease or prevent fouling within the equipment, e.g., pipes and heat exchangers, through which the steam cracker effluent can be conveyed or otherwise transported, e.g., to a separator for separation from the steam cracker effluent of the tar product and the upgraded steam cracker effluent. Those skilled in the art will appreciate that the amount of the quench fluid contacted with the steam cracker effluent should be sufficient to cool the steam cracker effluent to facilitate separation of the desired products, e.g., in a tar knock-out drum and/or a primary fractionator. Although the amount of quench fluid needed to do this can vary considerably from facility to facility, the quench fluid:steam cracker effluent weight ratio is typically in the range of from about 0.1 to about 10, e.g., 0.5 to 5, such as 1 to 4. The desired weight ratio in a particular instance can be determined, e.g., from factors such as the amount of steam cracker effluent to be cooled, the temperature of the steam cracker effluent at the quenching location, the composition and thermodynamic properties (e.g., enthalpy, $C_P$, etc.) of the quench fluid and the steam cracker effluent, the desired temperature of the quench fluid-steam cracker effluent mixture (namely the cooled steam cracker effluent) at the primary fractionator inlet, etc.

In certain aspects, the cooled steam cracker effluent can include the quench fluid in an amount of about 5 wt. % to about 95 wt. %, about 25 wt. % to about 90 wt. %, or about 50 wt. %, or about 80 wt. %, based on the weight of the cooled steam cracker effluent. In some examples, the quench fluid can be the utility fluid product or "first portion" of the utility fluid product. In other examples, the quench fluid can be a mixture of the first portion of the utility fluid product and one or more additional fluids. The quench fluid can typically be a mixture that can include at least a portion of the utility fluid product and optionally fuel oil, hydroprocessed tar, steam cracker naphtha, steam cracker gas oil, or any mixture thereof. Less commonly, the quench fluid includes or further includes water (e.g., steam) and other aqueous compounds. In some examples, the quench fluid can include the utility fluid product in an amount ≥10 wt. %, such as ≥25 wt. %, or ≥50 wt. %, or ≥75 wt. %, or in the range of about 25 wt. % to about 100 wt. %, or about 50 wt. % to about 100 wt. %; the weight percent values being based on a weight of the quench fluid. In some examples, the cooled steam cracker effluent can include the first portion of the utility fluid product in an amount of about 5 wt. % to about 95 wt. %, about 5 wt % to about 80 wt %, about 25 wt. % to about 90 wt. %, or about 50 wt. % to about 80 wt. %, based on the weight of the cooled steam cracker effluent. In other examples, the cooled steam cracker effluent can include about 5 wt. % to about 80 wt. %, about 10 wt % to about 75 wt %, about 15 wt % to about 70 wt %, or about 20 wt % to about 65 wt % of the utility fluid or the first portion of the utility fluid, based on a combined weight of the quench fluid and the steam cracker effluent.

It has also been surprisingly and unexpectedly discovered that the utility fluid product or "second portion" of the utility fluid product can be contacted with the steam cracker effluent or the cooled steam cracker effluent within a separator, e.g., a fractionator, used to separate process gas and other streams (e.g., SCN and/or SCGO) from the upgraded steam cracker effluent. Doing so can decrease or prevent fouling within the separator. In some examples, the cooled steam cracker effluent can be contacted with the second portion of the utility fluid product during separation of the tar product and the upgraded steam cracker effluent from the cooled steam cracker effluent at a weight ratio of the second portion of the utility fluid product to the cooled steam cracker effluent that is ≥0.01:1, e.g., ≥0.1:1, such as ≥1:1, or ≥5:1, or in the range of about 0.5:1 to about 4:1, or about 1:1 to about 4:1. The weight of the cooled steam cracker effluent equals the sum of the weight of the steam cracker effluent plus the weight of the quench fluid combined therewith.

In some examples, the quench fluid that can be or include the first portion of the utility fluid product can be contacted with the steam cracker effluent to produce the cooled steam cracker effluent and a "second portion" of the utility fluid product can be contacted with the cooled steam cracker effluent within the separator during separation of the tar product and the upgraded steam cracker effluent. The first portion of the utility fluid product, the second portion of the utility fluid product, and any other "portions", e.g., a third portion of the utility fluid product, can have the same or substantially the same composition as one another, e.g., as may be the case when these portions are divided or otherwise obtained from the same utility fluid source.

FIG. 1 depicts a schematic of an illustrative system 100 for steam cracking a vapor phase product (the first vapor phase product), catalytically cracking a liquid phase product (the first liquid phase product), and hydroprocessing a bottoms product separated from the catalytically cracked effluent to produce a hydroprocessed product, according to one or more embodiments. A hydrocarbon-containing feed, e.g., a feed containing $C_{5+}$ hydrocarbons, via line 101 and water, steam, or a mixture of water and steam via line 102 can be mixed, blended, combined, or otherwise contacted to produce a mixture via line 103. The mixture can include about 10 wt. % to about 95 wt. % of the water and/or steam, based on a combined weight of the hydrocarbon and the water and/or steam. In some examples, the hydrocarbon in line 101 that can be mixed, blended, combined, or otherwise contacted with the water and/or steam in line 102 to produce the mixture in line 103 can be or include the hydrocarbons or hydrocarbon feedstocks disclosed in U.S. Pat. Nos. 7,993,435; 8,696,888; 9,327,260; 9,637,694; 9,657,239; and 9,777,227; and International Patent Application Publication No. WO 2018/111574.

The mixture in line 103 can be heated, e.g., to a temperature of about 200° C. to about 585° C., to produce a heated mixture. For example, the mixture in line 103 can be heated in a convection section 105 of a furnace 104 to produce the heated mixture via line 107. Although the heating can be carried out to achieve a temperature of the mixture of line 103 in the range of about 340° C. to 550° C., the heating is typically carried out to achieve a mixture temperature in a range of from >400° C. to 550° C., e.g., 405° C. to 450° C., such as 410° C. to 425° C. A vapor phase product or "first vapor phase product" and a liquid phase product or "first liquid phase product" can be separated from the heated mixture by introducing the heated mixture via line 107 to one or more separators of a "first separation stage" 108. The first vapor phase product via line 109 and the first liquid phase product via line 110 can be recovered from the first separation stage 108, which is typically operated at a cut point >400° C. In some examples, the first liquid phase product can be sold as a product. For example, the first liquid phase product in line 110 can be conducted away, stored, and/or sold or used as a fuel oil (of relatively-high sulfur content, similar to that of conventional vacuum tower bottoms) or a fuel blending component. In other examples, the first liquid phase product in line 110 can be further processed. Although steam can be used to strip additional hydrocarbon from the first liquid phase product to the first vapor phase product, e.g., by introducing steam into a lower region of separation stage 108, this not required. In certain aspects such steam stripping is not carried out, e.g., to lessen the amount of fouling in the separation vessel. It is surprisingly found that steam stripping in the vapor-liquid separator can result in fouling and coke formation even at a vapor-liquid separator cut point in the range of from 200° C. to 400° C. Consequently, when the vapor-liquid separator cut point is in this range, the vapor-liquid separator is typically operated without steam stripping.

The liquid phase product or "first" liquid phase product via line 110 can be introduced to one or more catalytic crackers 112. Typically the catalytic cracker includes at least one riser reactor, for contacting the first liquid product with fluidized catalytic cracking catalyst, and at least one regenerator for regenerating the fluidized catalyst for re-use. Conventional fluidized catalytic cracking units are suitable, but the invention is not limited thereto. The first liquid phase product can be cracked in the presence of one or more fluidized catalysts to produce a catalytically cracked effluent via line 114. The catalytically cracked effluent via line 114 can be introduced to one or more separators of a "second separation stage" 116 and one, two, or more products can be separated therefrom. For example, one, two, or more of an FCC $C_{4-}$ product (a light hydrocarbon product) via line 117, and FCC naphtha via line 118, an FCC cycle oil via line 119, and a bottoms product via line 120 can be recovered from the second separator 116. The FCC $C_{4-}$ product typically includes $C_1$, $C_2$, $C_3$, and $C_4$ hydrocarbon, and in addition generally one or more of molecular hydrogen, ammonia, carbon dioxide, arsine, mercury, hydrogen sulfide, carbonyl sulfide, mercaptans, and carbon disulfide, oxygenates and water. The FCCU 112 can include additional equipment that is typically used in such a process, e.g., a separator such as a cyclone separator for separating the fluidized catalyst from the catalytically cracked effluent. It should also be understood that FCCU 112 can also include additional separators such as a catalyst fines separator configured to remove entrained catalyst particles from the bottoms product or other product(s) separated therefrom.

Although not shown, it should be understood that the first liquid phase product in line 110 can be subjected to one or more upgrading processes to produce an upgraded first liquid phase product that can be introduced to the fluidized catalytic cracker 112. For example, the first liquid phase product via line 110 can be introduced to one or more optional hydroprocessing units that can hydroprocess the liquid phase product in the presence of molecular hydrogen and a catalyst to produce a hydroprocessed first liquid phase product. In some examples, the first liquid phase product in line 110 can be upgraded prior to introduction to the fluidized catalytic cracker 112. Conventional gas oil hydroprocessing can be used when first liquid phase product comprises vacuum gas oil and/or atmospheric gas oil. Suitable process conditions include a pressure in the range of about 3000 kPa to about 10,000 kPa, a temperature in the range of about 310° C. to about 410° C., and a space velocity (LHSV) in the range of about 0.5 $hr^{-1}$ to 5 $hr^{-1}$. Suitable catalysts include KF 907, KF 905, KF 861, KF 851, and KF 780 (each available from Albemarle Corp., Houston, Tex.). Conventional resid hydroprocessing can be used when first liquid phase product comprises atmospheric resid and/or vacuum resid. Suitable process conditions include a pressure in the range of about 8000 kPa to about 20,000 kPa, a temperature in the range of about 350° C. to about 410° C., and a space velocity (LHSV) in the range of about 0.2 $hr^{-1}$ to 1.5 $hr^{-1}$. Suitable catalysts include FBR and EBR catalyst, also available from Albemarle Corp., Houston, Tex. The invention is not limited to these conventional catalysts and processes.

In some examples, the bottoms product via line 120 can be introduced into one or more stages of a pre-treater hydroprocessor 125 for pre-treating the bottoms product of line 120 under pre-treatment (also referred to as pre-treater) hydroprocessing conditions at a location upstream of one or more stages of a bottoms product hydroprocessor 130 for hydroprocessing the pre-treated bottoms in line 127. In other examples, as shown, at least a portion of the cycle oil via line or "first transfer line" 121 can optionally be mixed, blended, combined, or otherwise contacted with the bottoms product in line 120 to produce a bottoms product-cycle oil mixture or "fluxed bottoms" in line 122 that can be introduced to the pre-treater hydroprocessor 125. As such, the bottoms product via line 120 or the fluxed bottoms via line 122 and molecular hydrogen via line 123 can be introduced into the pre-treater hydroprocessor 125. The bottoms product or the fluxed bottoms can be hydroprocessed in the presence of the molecular hydrogen and a first catalyst, e.g., catalyst bed 126, under a first set of hydroprocessing conditions (pre-treater hydroprocessing conditions) to produce an intermediate or pre-treated product that can be conducted away via line 127.

Pre-treater hydroprocessing conditions can include a temperature $T_{PT} \leq 400°$ C., a space velocity (WHSV$_{PT}$) $\geq 0.2$ $hr^{-1}$, $\geq 0.25$ $hr^{-1}$, or $\geq 0.3$ $hr^{-1}$ based on the weight of the bottoms product of line 120 or the fluxed bottoms of line 122 that is subjected to the pre-treater hydroprocessing conditions, a total pressure ("$P_{PT}$") $\geq 3.5$ MPa, e.g., $\geq 6$ MPa, and supplying the molecular hydrogen at a rate <3000 standard cubic feet per barrel of the bottoms product of line 120 or the fluxed bottoms of line 122 that is subjected to the pre-treater hydroprocessing conditions (SCF/B) (534 S $m^3/m^3$).

The pre-treated product via line 127 and optionally molecular hydrogen via line 128 can be introduced to the bottoms product hydroprocessor 130. In some examples, in addition to or in lieu of introducing molecular hydrogen via line 128, molecular hydrogen can be cascaded from the pre-treater hydroprocessor 125 into the bottoms product hydroprocessor 130 with the pre-treated product via line 127. The pre-treated product can be hydroprocessed in the presence of the molecular hydrogen and a second catalyst, e.g., catalyst bed 131, to produce a hydroprocessed product via line 135. It should be understood that any number of hydroprocessing units and any number of hydroprocessing conditions can be used to produce the hydroprocessed product in line 135.

Bottoms product hydroprocessing conditions typically include a temperature ("$T_{BP}$") $\geq 200°$ C.; a total pressure ("$P_{BP}$") $\geq 3.5$ MPa, e.g., $\geq 6$ MPa; a weight hourly space velocity ("WHSV$_{BP}$") $\geq 0.2$ $hr^{-1}$, $\geq 0.25$ $hr^{-1}$, or $\geq 0.3$ $hr^{-1}$ based on the weight of the pre-treated product of line 127 subjected to the bottoms product hydroprocessing; and a total amount of molecular hydrogen supplied to the tar hydroprocessor that is $\geq 1000$ standard cubic feet per barrel of pre-treated product of line 127 subjected to the bottoms hydroprocessing (178 S $m^3/m^3$). Conditions can be selected within the bottoms product hydroprocessing conditions to achieve a 566° C.+ conversion of $\geq 20$ wt. % substantially continuously for at least ten days at a molecular hydrogen consumption rate of about 2200 standard cubic feet per barrel of bottoms product of line 120 or of bottoms product in the fluxed bottoms of line 122 (SCF/B) (392 S $m^3/m^3$) to about 3200 SCF/B (570 S $m^3/m^3$). In some examples, the pre-treater hydroprocessing conditions and the bottoms product hydroprocessing conditions can be the same or substantially similar to the pretreatment hydroprocessing and the intermediate hydroprocessing conditions disclosed in International Patent Application Publication No. WO 2018/111574.

The second hydroprocessed product via line 135 can be introduced to one or more separators of a "third separation stage" 140 and a vapor phase product or "second" vapor phase product via line 141 and a liquid phase product or "second" liquid phase product via line 142 can be conducted away therefrom. The second vapor phase product via line 141 can be introduced to one or more upgrading units 145, e.g., one or more amine towers. For example, fresh amine via line 146 can be introduced to the upgrading unit 145 and a rich amine via line 147 can be recovered therefrom. A regenerated treat gas, which can be or include molecular hydrogen, via line 148 can be compressed in one or more compressors 149 to produce at least a portion of the molecular hydrogen in line 123. In some examples, at least a portion of the regenerated treated gas via line 124 can be removed from the system 100 and/or introduced the optional hydroprocessing unit that can be used to hydroprocess the first liquid phase product in line 110 prior to introduction to the fluidized catalytic cracker 112.

The second liquid phase product via line 142 can be introduced to one or more separators of a "fourth separation stage" 150. Optionally, the functions of stages 140 and 150 can be carried out in one separation stage (not shown). In some examples, a hydroprocessor heavy product via line 151, an overhead or vapor via line 152, the utility fluid product via line 153 can be recovered from the separator of the fourth separation stage 150. In some examples, the hydroprocessor heavy product via line 151, overhead or vapor via line 152, and the utility fluid product via line 153 can be separated from the second liquid phase product according to the processes and systems disclosed in U.S. Pat. Nos. 9,090,836; 9,637,694; 9,777,227; and International Patent Application Publication No. WO 2018/111574. In certain aspects, the utility fluid of line 153 can include partially hydrogenated 2-4 ring molecules, such as dihydroanthracene and tetralin. These molecules can readily transfer hydrogen radicals to reactive free radicals in steam cracker effluent (e.g., of line 160) to make stable products. An exemplary equation for the radical transfer is shown below:

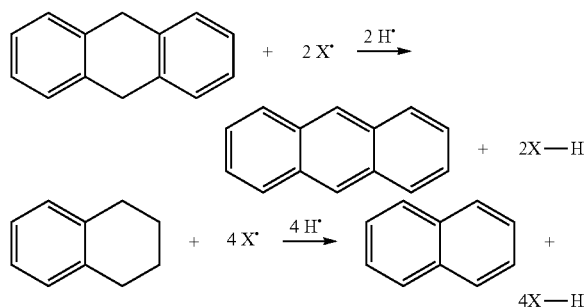

where X* refers to a radical species, and H* refers to a hydrogen radical. Since bottoms product and/or tar hydroprocessing can generate excess utility fluid (i.e., beyond that needed as a flux/solvent during bottoms hydroprocessing and/or tar hydroprocessing), at least a portion of the excess utility fluid can be used as a quench oil to quench the effluent flowing from a pyrolysis furnace and/or a transfer line exchanger ("TLE"). The relatively high temperature during quench facilitates hydrogen transfer from the utility fluid to the free radicals. The utility fluid can also be used to mix with various effluent streams flowing from a separation apparatus (e.g., a primary fractionator). The concentration of the donatable hydrogen in a sample of the utility fluid and other characteristics of the utility fluid are disclosed in U.S. Patent Application No. 62/716,754.

Returning to the first vapor phase product in line 109, the first vapor phase product can be introduced to a radiant section 106 of the furnace 104 to produce a steam cracker effluent, which can be conducted away via line 160. Typically, process conditions in stage 108 are selected to produce a first vapor phase product that is at a temperature ≥410° C. at the radiant section inlet, e.g., ≥420° C., such as a temperature in the range of about 425° C. to about 825° C. If needed, the first vapor phase product in line 109 can be heated in the convection section 105 of the furnace 104 prior to introducing the first vapor phase product to the radiant section 106 of the furnace 104. In some examples, additional water and/or steam can be mixed, blended, combined, or otherwise contacted with the first vapor phase product in line 109 before introducing the first vapor phase product to the radiant section 106 of the furnace 104 for steam cracking. In some examples, the first vapor phase product in line 109 can be steam cracked according to the processes and systems disclosed in U.S. Pat. Nos. 6,419,885; 7,993,435; 9,637,694; and 9,777,227; and International Patent Application Publication No. WO 2018/111574.

In some examples, the steam cracker effluent in line 160 can be mixed, blended, combined, or otherwise contacted with a quench fluid to produce a cooled steam cracker effluent. In one example, the steam cracker effluent in line 160 can be contacted with the utility fluid product or a "first portion" of the utility fluid product via line or "second transfer line" 154 to produce the cooled steam cracker effluent in line 162. In some examples, the steam cracker effluent in line 160 can be at a temperature of ≥300° C., ≥400° C., ≥500° C., ≥600° C., or ≥700° C., or ≥800° C., or more when initially contacted with the quench fluid in line 161. In certain aspects, to the greatest temperature of the steam cracker effluent in line 160 can be in the range of about 425° C. to 850° C., e.g., about 450° C. to about 800° C., when initially contacted with the quench fluid in line 161. As noted above, in lieu of or in addition to the first portion of the utility fluid product, one or more additional fluids can be used as the quench fluid, such as fuel oil, hydroprocessed tar, steam cracker naphtha, steam cracker gas oil, or any mixture thereof. In certain aspects, however, the quench fluid consists essentially of or consists of the utility fluid product. Typically, sufficient quench fluid of a sufficient temperature (optionally in combination with heat exchangers such as one or more TLEs) is used to produce a cooled steam cracker effluent having a temperature in a range that is typically from 250° C. to 850° C., e.g., 350° C. to 700° C., before separating a tar product and an upgraded steam cracker effluent. Typically, the quenching is carried out to decrease the temperature of the steam cracker effluent at the quench location (e.g., before and/or after a TLE) from an initial temperature $T_1$, e.g., in the range of 600° C. to 850° C., to a final temperature, $T_2$ e.g., in the range of 250° C. to 500° C. to slow down the reactions that lead to excessive coke and gas formation. Typically $T_1-T_2 \geq 100°$ C., e.g., ≥125° C., such as ≥150° C. The quenching typically results in the formation of a two-phase mixture, e.g., a mixture comprising (i) a vapor phase and (ii) a liquid phase containing steam cracker tar. The concentration of the donatable hydrogen in a sample of the utility fluid and other characteristics of the utility fluid are disclosed in U.S. Patent Application No. 62/716,754. Locations for carrying out the quenching are described in U.S. Patent Application Publication No. 2014/0061100, which is incorporated by reference herein in its entirety.

The steam cracker effluent via line 160 or, as shown, the cooled steam cracker effluent via line 162 can be introduced to one or more separators of a "fifth separation stage" 165. In some examples, a tar product via line 166 (e.g., obtained from primary fractionator bottoms and/or a tar knock-out drum located in stage 165) and one or more additional products, e.g., a process gas via line 167, steam cracker naphtha via line 168, and/or steam cracker gas oil via line 169, can be recovered from the separator of the fifth separation stage 165. In some examples, products that can be separated from the process gas in line 167 can include, but are not limited to, a tail gas, ethane, propane, crude $C_4$ hydrocarbons, or any combination thereof. The fifth separation stage 165 can be or include one or more fractionators, knockout drums, a combined quench tower and primary fractionator, a compressor, contaminant removal units, e.g., $CO_2$ and/or $H_2S$ removal units, acetylene converter, etc. In some examples, the products that can be separated from the steam cracker effluent or the cooled steam cracker effluent can be separated according to the processes and systems disclosed in U.S. Patent Application Publication No. 2014/0357923.

In some examples, the steam cracker effluent or, as shown, the cooled steam cracker effluent can be contacted with the utility fluid product or a "second portion" of the utility fluid product via line or "third transfer line" 156 during separation of the tar product via line 166 and the one or more additional products. In some examples, the second portion of the utility fluid product via line 156 can be introduced to a reflux or bottoms pump around ("BPA") line 163 recovered and recycled to the separator of the fifth separation stage 165. In other examples, the second portion of the utility fluid product via line 156 can be introduced directly to the separator of the fifth separation stage 165. Heat transfer stage 177 can be used to regulate the temperature of the bottoms, adding or removing heat to/from the BPA as needed to (i) maintain stage 165 (particularly a primary fractionator in stage 165) operating as desired and (ii) to maintain primary fractionator bottoms at a temperature and residence time sufficient to transfer hydrogen from the utility fluid product to the bottoms.

In some examples, the tar product via line 166 can be mixed, blended, combined, or otherwise contacted with the bottoms product in line 120 or the fluxed bottoms in line 122 to produce a bottoms product-tar mixture or a fluxed mixture that further includes the tar product that can be introduced into the first stage hydroprocessing unit 125 to produce the pre-treated product recovered via line 127. In some examples, the tar product in line 166 can be mixed, blended, combined, or otherwise contacted with a diluent, e.g., the utility fluid product or a "third portion" of the utility fluid product, via line or "fourth transfer line" 153 to produce a tar product-diluent mixture in line 171, which can also be referred to as a tar product-utility fluid mixture. In some examples, the tar product-diluent mixture via line 171 can be mixed, blended, combined, or otherwise contacted with the bottoms product in line 120 to produce a bottoms product-utility fluid-diluent mixture. In other examples, the tar product-diluent mixture via line 171 can be mixed, blended, combined, or otherwise contacted with the fluxed bottoms in line 122. As such, in some examples, the fluxed bottoms in line 122 can include the bottoms product, the cycle oil, and at least one of the tar product and the diluent. In still other examples, the tar product-diluent mixture via line 171 can be directly introduced to the first stage hydroprocessing unit 125 (the pretreater), introduced into another treatment unit, e.g., another hydroprocessing unit, and/or removed from the system 100. In other examples, the tar product can be hydroprocessed in one or more additional hydroprocessing units or removed via line 170 from the system 100. Considering the appreciable compositional differences between steam cracker tar and the bottoms product or fluxed bottoms (e.g., the greater olefin and vinyl aromatic content in steam cracker tar compared to the bottoms product), it was expected that these streams would be incompatible, and co-processing them in stages 125 or 130 would lead to fouling, e.g., in beds 126 and/or 131. It is therefore surprising that this is not the case.

Figure 2:
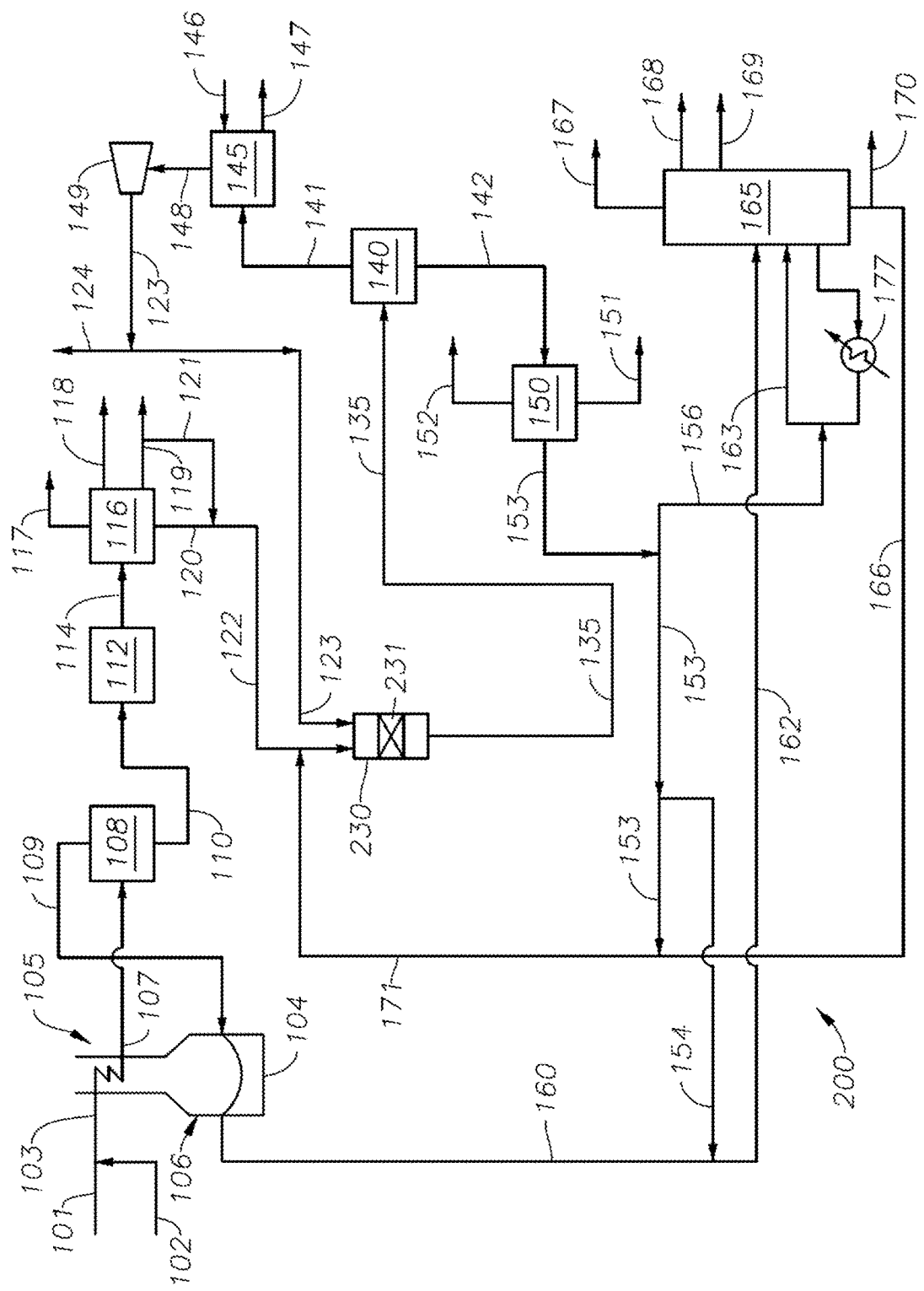
FIG. 2 depicts a schematic of an illustrative system for steam cracking a vapor phase product, catalytically cracking a liquid phase product, and hydroprocessing a fluxed bottoms that includes a bottoms product and a cycle oil separated from the catalytically cracked effluent to produce a hydroprocessed product, according to one or more embodiments described.

FIG. 2 depicts a schematic of an illustrative system for steam cracking a first vapor phase product, catalytically cracking a first liquid phase product, and hydroprocessing a fluxed bottoms that includes a bottoms product and a cycle oil separated from the catalytically cracked effluent to produce a hydroprocessed product, according to one or more embodiments. The system 200 can be similar to the system 100, but can include one or more bottoms product hydroprocessor 230. It should be understood, however, that the system 100 can include one or more pre-treater hydroprocessors 125 and one or more bottoms hydroprocessors 130 similar to system 100.

It has been surprisingly and unexpected discovered that the cycle oil in line 119 can be mixed, blended, combined, or otherwise contacted via first transfer line 121 with the bottoms product 120 to produce a bottoms-product-cycle oil mixture or "fluxed bottoms" via line 222 for hydroprocessing long-term without an undue increase in hydroprocessor pressure drop. The fluxed bottoms via line 222 can be introduced into one or more stages of the bottoms product hydroprocessor 230. The fluxed bottoms can be can he hydroprocessed in the presence of molecular hydrogen introduced via line 123 and a catalyst, e.g., catalyst bed 231, to produce the hydroprocessed product via line 135. The bottoms product hydroprocessor 230 and the operating conditions therein can be the same or substantially similar to the bottoms product hydroprocessor 130. In certain aspects, at least one hydroprocessing stage includes slurry hydroprocessing, e.g., in aspects where the cut point of vapor-liquid separation stage 108 is >400° C., e.g., ≥410° C. Conventional slurry hydroprocessing can be used, but the invention is not limited thereto.

The hydroprocessed product conducted away via line 135 from the bottoms hydroprocessor 230 can be further processed as discussed and described above with reference to FIG. 1. For example, a hydroprocessor heavy product via line 151, an overhead via line 152, and a utility fluid via line 153 can be recovered from one or more separators of the "fourth separation stage" 150.

It has been discovered that the utility fluid product is a hydrogen donor that can bind with fouling precursors in the steam cracker effluent, the bottoms product, and/or the tar product to decrease or prevent foulant formation during transport thereof. It has also been discovered that the utility fluid product is a hydrogen donor that can also decrease or prevent fouling in a primary separation stage, e.g., within one or more separators of the fifth separation stage 165. It was also discovered that the hydrogen donor properties of the utility fluid product make it an improved solvent for use in hydroprocessing the bottoms product and/or the tar product.

As used herein, the terms "utility fluid" and "utility fluid product" are used interchangeably and refer to a hydrocarbon composition that includes, but is not limited to, aromatic ring compounds. In some examples, the utility fluid product can include aromatic ring compounds and non-aromatic ring compounds. In some examples, the utility fluid product can be or include aromatic ring compounds or aromatic ring compounds and non-aromatic ring compounds, in an amount of ≥10 wt. %, ≥20 wt. %, ≥30 wt. %, ≥40 wt. %, ≥50 wt. %, ≥60 wt. %, ≥70 wt. %, ≥80 wt. %, ≥90 wt. %, ≥95 wt. %, or ≥98 wt. %, based on a weight of the utility fluid product. In some examples, the utility fluid product can include ≥10 wt. %, ≥20 wt. %, ≥30 wt. %, ≥40 wt. %, ≥50 wt. %, ≥60 wt. %, ≥70 wt. %, ≥80 wt. %, ≥90 wt. %, ≥95 wt. %, or ≥99 wt. % of aromatic ring compounds, based on the weight of the utility fluid product. The aromatic ring compounds can be or include 1-ring aromatic compounds, 2-ring aromatic compounds, 3-ring aromatic compounds, or any mixture thereof. The amount of aromatic ring compounds can be determined by Nuclear Magnetic Resonance, (e.g., $^{13}C$ NMR). Suitable methods for analyzing the aromatic and non-aromatic content of the utility fluid product are disclosed in U.S. Pat. No. 9,777,227 and in U.S. Patent Application Ser. No. 62/716,754.

In certain aspects, the utility fluid product can include from 0.5 to 7.0 ring class compounds, e.g., one or more of 0.5, 1.0, 1.5, 2.0, 2.5, 3.0, 3.5, 4.0, 4.5 ring class compounds. Typically, the utility fluid product comprises ≤0.1 wt. %, e.g., ≤0.05 wt. %, such as ≤0.01 wt. % total of 5.5, 6.0, 6.5, and 7.0 ring class compounds, based on the weight of the utility fluid product. Although other utility fluid products are within the scope of the invention, certain utility fluid products comprise, consist essentially of, or even consists of from 0.5 to 5.0 ring class compounds, e.g., 1.0 to 3.0 ring class compounds, such as 1.5 to 3.0 ring class compounds. In some examples, the utility fluid product can be or include, but is not limited to, (a)≥1 wt. % of 1.0 ring class compounds; (b)≥5 wt. % of 1.5 ring class compounds; and (c)≥5 wt. % of 2.0 ring class compounds, where all weight percent values are based on a weight of the utility fluid product. In other examples, the utility fluid product can be or include, but is not limited to, (a)≥1 wt. % to about 20 wt. % of 1.0 ring class compounds; (b)≥25 wt. % to about 95 wt. % of 1.5 ring class compounds; (c)≥5 wt. % to about 80 wt. % of 2.0 ring class compounds; and (d)≥0.01 wt. % to about 0.5 wt. % of 5.0 ring class compounds, where all weight percent values are based on a weight of the utility fluid product. In certain aspects the utility fluid product comprises 1 wt. % to 10 wt. % of 1.0 ring class compounds, about 30 wt. % to 60 wt. % of 1.5 ring class compounds, and about 10 wt. % to 40 wt. % of 2.0 ring class compounds. Optionally, the utility fluid comprises ≤1.0 wt. % of 4.0 ring class compounds, e.g., 0.01 wt. % to 1 wt. %; and/or ≤1.0 wt. % of 3.0 ring class compound, e.g., 0.1 wt. % to 1 wt. %. It is generally desirable for the utility fluid product to be substantially free of molecules having terminal unsaturation, for example, vinyl aromatics. The term "substantially free" in this context means that the utility fluid comprises ≤10.0 wt. % (e.g., ≤5.0 wt. % or ≤1.0 wt. %) vinyl aromatics, based on the weight of the utility fluid.

As used herein, the term "0.5 ring class compound" means a molecule having only one non-aromatic ring moiety and no aromatic ring moieties in the molecular structure. As used herein, the term "non-aromatic ring" means four or more carbon atoms joined in at least one ring structure where at least one of the four or more carbon atoms in the ring structure is not an aromatic carbon atom. Aromatic carbon atoms can be identified using $^{13}C$ Nuclear magnetic resonance, for example. Non-aromatic rings having atoms attached to the ring (e.g., one or more heteroatoms, one or more carbon atoms, etc.), but which are not part of the ring structure, are within the scope of the term "non-aromatic ring".

Examples of non-aromatic rings include a pentacyclic ring-five carbon member ring such as cyclopentane and a hexacyclic ring-six carbon member ring such as cyclohexane. It should be understood that the non-aromatic ring can be statured as exemplified above or partially unsaturated for example, cyclopentene, cyclopentadiene, cyclohexene and cyclohexadiene. Non aromatic rings, which can primarily be six and five member non-aromatic rings, can contain one or more heteroatoms such as sulfur (S), nitrogen (N) and oxygen (O). Illustrative non-aromatic rings with heteroatoms can be or include, but are not limited to, tetrahydrothiophene, pyrrolidine, tetrahydrofuran, tetrahydro-2H-thiopyran, piperidine, and tetrahydro-2H-pyran. It should be understood that the non-aromatic rings with hetero atoms can be saturated or partially unsaturated.

As used herein, the term "1.0 ring class compound" means a molecule containing only one of the following ring moieties but no other ring moieties: (i) one aromatic ring 1•(1.0 ring) in the molecular structure, or (ii) two non-aromatic rings 2•(0.5 ring) in the molecular structure. As used herein, the term "aromatic ring" means five or six atoms joined in a ring structure where: (i) at least four of the atoms joined in the ring structure are carbon atoms, and (ii) all of the carbon atoms joined in the ring structure are aromatic carbon atoms. It should be understood that aromatic rings having atoms attached to the ring, e.g., one or more heteroatoms, one or more carbon atoms, etc., but which are not part of the ring structure are within the scope of the term "aromatic ring". Illustrative aromatic rings can be or include, but are not limited to, (i) a benzene ring such as benzene; (ii) a thiophene ring such as thiophene; (iii) a pyrrole ring such as 1H-pyrrol; and (iv) a furan ring such as furan.

When there is more than one ring in a molecular structure, the rings can be aromatic rings and/or non-aromatic rings. The ring to ring connection can be of two types: type (1) where at least one side of the ring is shared, and type (2) where the rings are connected with at least one bond. The type (1) structure is also known as a fused ring structure. The type (2) structure is also commonly known as a bridged ring structure. Some examples of the type (1) fused ring structure include, but are not limited to, naphthalene; 1,2,3,4-tetrahydronaphthalene; decahydronaphthalene, indane; and octahydropentalene. An example of the type (2) bridged ring structure can be as follows:

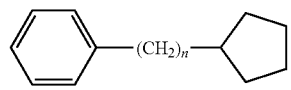

where n is an integer equal to 0, 1, 2, or 3. When there are two or more rings (aromatic rings and/or non-aromatic rings) in a molecular structure, the ring to ring connection may include all type (1) connections, all type (2) connections, or a mixture of types (1) connections and type (2) connections.

As used herein, the term "1.5 ring class compound" means a molecule containing only one of the following ring moieties, but no other ring moieties: (i) one aromatic ring 1•(1.0 ring) and one non-aromatic ring 1•(0.5 ring) in the molecular structure or (ii) three non-aromatic rings 3•(0.5 ring) in the molecular structure. As used herein, the term "2.0 ring class compound" means a molecule containing only one of the following ring moieties, but no other ring moieties: (i) two aromatic rings 2•(1.0 ring), (ii) one aromatic ring 1•(1.0 ring) and two non-aromatic rings 2•(0.5 ring) in the molecular structure, or (iii) four non-aromatic rings 4•(0.5 ring) in the molecular structure. As used herein, the term "2.5 ring class compound" means a molecule containing only one of the following ring moieties, but no other ring moieties: (i) two aromatic rings 2•(1.0 ring) and one non-aromatic rings 1•(0.5 ring) in the molecular structure, (ii) one aromatic ring 1•(1.0 ring) and three non-aromatic rings 3•(0.5 ring) in the molecular structure, or (iii) five non-aromatic rings 5•(0.5 ring) in the molecular structure. Likewise compounds of the 3.0, 3.5, 4.0, 4.5, 5.0, etc. molecular classes contain a combination of non-aromatic rings counted as 0.5 ring and aromatic rings counted as 1.0 ring, such that the total is 3.0, 3.5, 4.0, 4.5, 5.0, 5.5, 6.0, 6.5, 7.0, etc. respectively. For example, 5.0 ring class compounds contain only one of the following ring moieties, but no other ring moieties: (i) five aromatic rings 5•(1.0 ring) in the molecular structure, (ii) four aromatic rings 4•(1.0 ring) and two non-aromatic rings 2•(0.5 ring) in the molecular structure, (iii) three aromatic rings 3•(1.0 ring) and four non-aromatic rings 4•(0.5 ring) in the molecular structure, (iv) two aromatic rings 2•(1.0 ring) and six non-aromatic rings 6•(0.5 ring) in the molecular structure, (v) one aromatic ring 1•(1.0 ring) and eight non-aromatic rings 8•(0.5 ring) in the molecular structure, or (vi) ten non-aromatic rings 10•(0.5 ring) in the molecular structure. It should be understood that all of the multi-ring classes can include ring compounds having hydrogen, alkyl, or alkenyl groups bound thereto, e.g., one or more of H, $CH_2$, $C_2H_4$ through $C_nH_{2n}$, $CH_3$, $C_2H_5$ through $C_nH_{2n+1}$. Generally, n is from 1 to 6, e.g., from 1 to 5.

The utility fluid product can include 0.5, 1.0, 1.5, 2.0, 2.5, 3.0, 3.5, 4.0, and/or 4.5 ring class compounds. The utility fluid product can further include 0.1 wt. % or less, 0.05 wt. % or less, or 0.01 wt. % or less of 5.0 ring class compounds, based on the weight of the utility fluid product. In some examples, the utility fluid product can include 0.1 wt. % or less, 0.05 wt. % or less, or 0.01 wt. % or less of a total amount of 5.5, 6.0, 6.5, and 7.0 ring class compounds, based on the weight of the utility fluid product. In some examples, the utility fluid product can include 0.5 to 7.0 ring class compounds. In other examples, the utility fluid product can include 0.5 to 5.0 ring class compounds. In other examples, the utility fluid product can include 1.0 to 3.0 ring class compounds.

In some examples, the utility fluid product can be or include about 1 wt. % to about 20 wt. % of 1.0 ring class compounds, about 5 wt. % to about 60 wt. % of 1.5 ring class compounds, and about 5 wt. % to about 60 wt. % of 2.0 ring class compounds, where all weight percent values are based on the weight of the utility fluid product. In other examples, the utility fluid product can include about 5 wt. % to about 22 wt. % of 1.0 ring class compounds, about 15 wt. % to about 80 wt. % of 1.5 ring class compounds, and about 10 wt. % to about 80 wt. % of 2.0 ring class compounds, where all weight percent values are based on the weight of the utility fluid product. In other examples, the utility fluid product can include about 5 wt. % to about 20 wt. % of 1.0 ring class compounds, about 35 wt. % to about 60 wt. % of 1.5 ring class compounds, and about 20 wt. % to about 80 wt. % of 2.0 ring class compounds. In other examples, the utility fluid product can include one or more of (i) 20 wt. % or less of 1.0 ring class compounds, (ii) 1 wt. % or less of 4.0 ring class compounds, and (iii) 1 wt. % or less of 3.0 ring class compounds, where all weight percent values are based on the weight of the utility fluid product.

The utility fluid product can have a 10% distillation point of ≥60° C. and a 90% distillation point of 350° C. or less, as measured according to ASTM D86-17. In some examples, the utility fluid product can have a 10% distillation point of ≥120° C., e.g., ≥140° C. or ≥150° C., and/or a 90% distillation point of 300° C. or less, as measured according to ASTM D86-17. The utility fluid product can have a critical temperature of about 285° C. to about 400° C. and include aromatics, including alkyl-functionalized derivatives thereof. The utility fluid product can have a high solvency, as measured by solubility blending number ("$S_{BN}$"). In some examples, the utility fluid product can have an $S_{BN}$ of about 90, about 100, or about 110 to about 120, about 130, or about 140. The $S_{BN}$ is a parameter that relates to the compatibility of an oil with different proportions of a model solvent mixture, such as toluene/n-heptane. The $S_{BN}$ is related to the insolubility number ("IN"), which can be determined in a similar manner, as disclosed in U.S. Pat. No. 5,871,634.

In some examples, the utility fluid product can include ≥90 wt. % of a single-ring aromatic, including those having one or more hydrocarbon substituents, such as from 1 to 3 or 1 to 2 hydrocarbon substituents. Illustrative hydrocarbon substituents or hydrocarbon groups can be or include, but are not limited to, $C_1$-$C_6$ alkyls, where the hydrocarbon groups can be branched or linear and the hydrocarbon groups can be the same or different. In some examples, the utility fluid product can include ≥90 wt. % of one or more of benzene, ethylbenzene, trimethylbenzene, xylenes, toluene, naphthalenes, alkylnaphthalenes (e.g., methylnaphthalenes), tetralins, or alkyltetralins (e.g., methyltetralins), based on the weight of the utility fluid product.

In some examples, the utility fluid product can be substantially free of molecules having terminal unsaturates, for example, vinyl aromatics. As used herein, the term "substantially free" means that the utility fluid product includes 10 wt. % or less, e.g., 5 wt. % or less or 1 wt. % or less, of terminal unsaturates, based on the weight of the utility fluid product. The utility fluid product can include ≥50 wt. % of molecules having at least one aromatic core, e.g., ≥60 wt. % or ≥70 wt. %, based on the weight of the utility fluid product. In some examples, the utility fluid product can include ≥60 wt. % of molecules having at least one aromatic core and 1 wt. % or less of terminal unsaturates, e.g., vinyl aromatics, based on the weight of the utility fluid product.

In some examples, the utility fluid product can include aromatic ring compounds and have a 10% distillation point of ≥60° C. and a 90% distillation point of 425° C. or less, as measured according to ASTM D86-17. In some examples, the utility fluid product can include ≥25 wt. % of aromatic ring compounds, based on the weight of the utility fluid product and can have a $S_{BN}$ of ≥100, or ≥120, ≥130, or ≥140, such as about 110 to about 155, or about 120 to about 150. In these and other examples, the utility fluid product can have a true boiling point distribution having an initial boiling point of ≥177° C. and a final boiling point of 566° C. or less, e.g., 430° C. or less. True boiling point distributions (the distribution at atmospheric pressure) can be measured according to ASTM D7500-15. In some examples, the utility fluid product can include aromatic ring compounds, have a 10% distillation point of ≥60° C. and a 90% distillation point of 350° C. or less, as measured according to ASTM D86-17, have a critical temperature of about 285° C. to about 400° C., and include ≥80 wt. % of 1-ring aromatics and/or 2-ring aromatics, including alkyl-functionalized derivatives thereof, based on a weight of the utility fluid product. In other examples, the utility fluid product can include aromatic ring compounds, have a 10% distillation point of ≥60° C. and a 90% distillation point of 350° C. or less, as measured according to ASTM D86-17, have a critical temperature of about 285° C. to about 400° C., and include ≥80 wt. % of 1-ring aromatics, 2-ring aromatics, and 3-ring aromatics including alkyl-functionalized derivatives thereof, based on a weight of the utility fluid product.

As noted above, the utility fluid product can be produced by hydroprocessing the bottoms product separated from the catalytically cracked effluent and/or the tar product separated from the cooled steam cracker effluent. In some examples, the utility fluid product can be the same or similar to the utility fluids disclosed in U.S. Pat. Nos. 9,090,836; 9,637,694; and 9,777,227; and International Patent Application Publication No. WO 2018/111574. It should be understood that the utility fluid product can be produced via any suitable process. In some examples, one or more aromatic ring compounds or one or more aromatic ring compounds and one or more non-aromatic ring compounds can be mixed, blended, combined, or otherwise contacted to produce the utility fluid product having the composition disclosed herein.

The composition of the utility fluid product can be determined using any suitable test method or combination of test methods. In some examples, conventional methods can be used to determine the types and amounts of compounds in the multi-ring classes disclosed above in the utility fluid product (and other compositions), though any method can be used. For example, it has been found that two-dimensional gas chromatography ("2D GC") is a convenient methodology for performing a quantitative analysis of samples of tar, hydroprocessed product, and other streams and mixtures. These methods for identifying the types and amounts of compounds are not meant to foreclose other methods for identifying molecular types and amounts, e.g., other gas chromatography/mass spectrometry (GC/MS) techniques. Methods for determining the composition of the utility fluid product can include those disclosed in U.S. Pat. No. 9,777,227.

As noted above, it has been discovered that the utility fluid product is a hydrogen donor that can that can bind with fouling precursors in the steam cracker effluent to decrease or prevent foulant formation. It has also been discovered that the utility fluid product is a hydrogen donor that can also decrease or prevent fouling in a primary separation stage, e.g., within one or more separator(s) of the second separation stage 112. It was also discovered that the hydrogen donor properties of the utility fluid product make it an improved solvent for use in hydroprocessing the tar product.

In some examples, the utility fluid product can be contacted with the steam cracker effluent and/or the cooled steam cracker effluent prior to (e.g., as a quench fluid or quench fluid component) and/or during separation of products therefrom, when the steam cracker effluent and/or the cooled steam cracker effluent is at a temperature of ≥300° C., ≥325° C., ≥350° C., ≥375° C., or ≥400° C. to about 425° C., to about 450° C., to about 475° C., or to about 500° C. Without wishing to be bound by theory, it is believed that at elevated temperature the steam cracker effluent and/or the cooled steam cracker effluent contain significant reactive molecules. The utility fluid contains hydrogen radicals that promotes or otherwise improves the rate of hydrogen donation from the utility fluid to the steam cracker effluent stream, e.g., the donation of a hydrogen atom or ion, from the utility fluid product to foulant forming constituents in the steam cracker effluent or the cooled steam cracker effluent, which can decrease or even prevent fouling. Advantageously, the utility fluid produced by the bottoms hydroprocessing can be used as a quench oil composition at various points upstream of the bottoms hydroprocessor to lessen and/or eliminate reactor fouling. Without being bound by theory, it is believed that the reduction in (or elimination of) reactor fouling is due to the hydrogen donating ability of the utility fluid composition. Hydrogen radicals transfer from the utility fluid to reactive radicals in various effluent streams, thereby mitigating olefin polymerization and minimizing or eliminating primary fractionator fouling. Since they also contain hydrogen-donor compounds, the second liquid phase product and the hydroprocessor heavy product are also useful as quench oil instead of or in addition to utility fluid.

Advantageously, the various utility fluid product streams can be used to mitigate fouling in downstream processing equipment in a stream cracker, such as the primary fractionator. Moreover, the yield of the product is better. Uncontrolled reactions involving reactive radicals, in conventional processes, lead to polymerization and/or coking, which lead to heavier products such as tar, coke, and fuel gas.

Returning again to FIGS. 1 and 2, the hydrocarbon feed introduced to furnace 104 via line 101 will now be described in more detail. The invention is not limited to these feeds, and this description is not meant to foreclose the use of other feeds within the broader scope of the invention.

The one or more hydrocarbons that can be mixed, blended, combined, or otherwise contacted with water, steam, or a mixture thereof and heated to produce the heated mixture can include any one or more of a number of hydrocarbons. In some examples, the hydrocarbon can include $C_{5+}$ hydrocarbons. Feeds or hydrocarbon feeds that include $C_{5+}$ hydrocarbons that can be mixed, blended, combined, or otherwise contacted with the water and/or steam and heated to produce the heated mixture can be or include, but is not limited to, raw crude oil, steam cracked gas oils and residues, gas oils, heating oil, jet fuel, diesel, kerosene, gasoline, coker naphtha, steam cracked naphtha, catalytically cracked naphtha, hydrocrackate, reformate, raffinate reformate, Fischer-Tropsch liquids, Fischer-Tropsch gases, natural gasoline, distillate, virgin naphtha, atmospheric pipestill bottoms, vacuum pipestill streams such as vacuum pipestill bottoms and wide boiling range vacuum pipestill naphtha to gas oil condensates, heavy non-virgin hydrocarbons from refineries, vacuum gas oils, heavy gas oil, naphtha contaminated with crude, atmospheric residue, heavy residue, $C_4$'s/residue admixture, naphtha/residue admixture, hydrocarbon gases/residue admixture, hydrogen/residue admixtures, waxy residues, gas oil/residue admixture, or any mixture thereof. In other examples, the hydrocarbon can be or include, naphtha, gas oil, vacuum gas oil, waxy residues, atmospheric residues, residue admixtures, crude oil, or any mixture thereof. In some examples, if the hydrocarbon feed (or preheated hydrocarbon feed) comprises, consists essentially of, or even consists of a primarily liquid phase hydrocarbon feed, e.g., a medium or heavy hydrocarbon. "Primarily liquid phase" in this context means a composition of which ≥50 wt. % is in the liquid phase, e.g., ≥75 wt. %, such as ≥90 wt. %. A hydrocarbon feed is a primarily liquid-phase hydrocarbon feed when ≥50 wt. % of the hydrocarbon feed is in the liquid phase at a temperature of 25° C. and a pressure of 1 bar absolute, e.g., ≥75 wt. %, such as ≥90 wt. %. "Heavy hydrocarbon" means a mixture comprising hydrocarbon, the mixture having an API gravity in the range of from 5° up to (but not including) 22°. "Medium hydrocarbon" means a mixture comprising hydrocarbon, the mixture having an API gravity in the range of from 22° to 30°. A "relatively-heavy" hydrocarbon has an API gravity that is less than that of naphtha. The hydrocarbon feed can be a raw feed such as crude oil. "Raw" feed, e.g., raw hydrocarbon feed, means a primarily liquid-phase feed that comprises ≥25 wt. % of crude oil that has not been subjected to prior desalting and/or prior fractionation with reflux, e.g., ≥50 wt. %, such as ≥75 wt. %, or ≥90 wt. %. "Crude oil" means a mixture comprising naturally-occurring hydrocarbon of geological origin, where the mixture (i) comprises ≥1 wt. % of resid, e.g., ≥5 wt. %, such as ≥10 wt. %, and (ii) has an API gravity ≤52°, e.g., ≤30°, such as ≤20°, or ≤10°, or ≤8°. The crude oil can be classified by API gravity, e.g., heavy crude oil has an API gravity in the range of from 5° up to (but not including) 22°, e.g., from 5° to 20°. Surprisingly, it has been found that for a wide range of raw heavy crude oil feeds, that operating the steam cracking furnace with an integrated a vapor-liquid separator having a cut point in the narrow range of 510° C. to 566° C., or 523° C. to 542° C., that utilizing the specified utility fluid as the quench fluid results in a number of improvements over prior art hydrocarbon conversion processes. Among these improvements are one or more of (i) an increase in process gas yield, (ii) a decrease in the amount of hydroprocessed heavy product, and (iii) an improvement in certain properties of the hydroprocessed heavy tar product including a viscosity decrease, improved blending characteristics, and a decrease in vinyl aromatic content. In these and certain other aspects the quench fluid is substantially free of primary fractionator bottoms.

Although it is not required, the crude oil can be desalted prior to contacting with the water and/or steam to form the mixture. When the hydrocarbon feed includes a crude oil fraction, the fraction can be produced by separating atmospheric pipestill ("APS") bottoms from the crude oil followed by vacuum pipestill ("VPS") treatment of the APS bottoms. In some examples, the hydrocarbon feed can be or include a crude oil such as a high-sulfur virgin crude oil rich in polycyclic aromatics or a fraction thereof. In other examples, the hydrocarbon feed can be or include a hydroprocessed hydrocarbon, e.g., a crude or resid-containing fraction thereof. In other examples, the hydrocarbon feed can be or include a vapor phase separate from a vacuum resid subjected to a thermal conversion process in a thermal conversion reactor, e.g., a delayed coker, a fluid coker, a flex-coker, a visbreaker, and/or a catalytic hydrovisbreaker). In some examples, the hydrocarbon feed can be or include the hydrocarbons or hydrocarbon feedstocks disclosed in U.S. Pat. Nos. 7,993,435; 8,696,888; 9,327,260; 9,637,694; 9,657,239; and 9,777,227; and International Patent Application Publication No. WO 2018/111574.

The heated mixture that includes the $C_{5+}$ hydrocarbons and the water and/or steam can include about 10 wt. %, about 20 wt. %, or about 30 w % to about 70 wt. %, about 80 wt. %, about 90 wt. %, or about 95 wt. % of the water and/or steam, based on a combined weight of the hydrocarbon and the water and/or steam. In certain aspects, the heating is carried out to achieve a mixture temperature in the range of from 330° C. to 585° C., e.g., 340° C. to 550° C., such as from >400° C. to 550° C., e.g., 405° C. to 450° C., or 410° C. to 425° C. In other aspects the mixture is heated to achieve a temperature of about 410° C., about 425° C., about 450°, about 475° C., about 500° C., about 515° C., or about 530° C. to about 540° C., about 555° C., about 565° C., or about 585° C., or at any temperature between a pair of these temperatures. The vapor phase product (in certain aspects, the first vapor phase product) and the liquid phase product (in certain aspects, the first liquid phase product) can be separated from the heated mixture, e.g., via one or more flash drums or other separator(s). In some examples, the liquid phase product can include hydrocarbons having a minimum boiling point ≥350° C., e.g., in a range of about 500° C. to about 570° C., about 520° C. to about 550° C., or about 530° C. to about 545° C., as measured according to ASTM D6352-15 or ASTM D2887-16a. Those skilled in the art will appreciate that should an indicated boiling point fall outside the range specified in one or more of these standards, it can be determined by extrapolation. In certain aspects, the liquid phase product can include hydrocarbons having a minimum boiling point of about 405° C., about 410° C., about 425° C., about 450°, about 475° C., about 500° C., about 515° C., or about 530° C. to about 540° C., about 555° C., about 565° C., or about 585° C., or at any temperature between a pair of these temperatures. A surprising number of desirable process and product features result from heating the mixture and operating the vapor-liquid separator to produce a first liquid phase product having a minimum boiling point >400° C., e.g., in a range of from >400° C. to 550° C., such as from 405° C. to 450° C., or 410° C. to 425° C. These desirable features include one or more of (i) improved compatibility of the tar product and bottoms product when combined for the pretreatment hydroprocessing (e.g., without appreciable asphaltene precipitation), (ii) improved yields of naphtha boiling-range products of the catalytic cracking without a need for hydroprocessing the first liquid phase product, (iii) improved yield of the utility fluid product, and (iv) an improvement in certain properties of the hydroprocessor heavy product including a viscosity decrease, improved blending characteristics, and a decrease in vinyl aromatic content. Although these features are achieved for a wide range of hydrocarbon feeds, they are especially important when utilizing a feed comprising medium or heavy hydrocarbon, e.g., a heavy crude oil feed having an API gravity in a range of from 5° to 20° (e.g., a raw heavy crude oil feed in this API gravity range).

Typically, at least part of the heating of the hydrocarbon feed, the aqueous diluent, and/or the mixture thereof is carried out via indirect heating in one or more coils located in a steam cracking furnace, generally in coils located in the furnace's convection section. It is also typical to separate the first liquid phase product and the first vapor phase product from the heated mixture in one or more vapor-liquid separators integrated with the steam cracking furnace, e.g., integrated with the convection section of the steam cracking furnace. In some examples, the heated mixture can be produced and the vapor phase product and the liquid phase product can be separated therefrom according to the processes and systems disclosed in U.S. Pat. No. 7,993,435. Some illustrative vapor/liquid separation devices and separation stages that can be used to separate the vapor phase product and the liquid phase produce from the heated mixture can also include those disclosed in U.S. Pat. Nos. 7,138,047; 7,090,765; 7,097,758; 7,820,035; 7,311,746; 7,220,887; 7,244,871; 7,247,765; 7,351,872; 7,297,833; 7,488,459; 7,312,371; 6,632,351; 7,578,929; and 7,235,705.

Typically, the first separation stage is configured so that the first vapor phase product has a normal boiling point range ≤425° C., e.g., ≤about 370° C. For example, the first vapor phase product can have a normal boiling point in a range from the normal boiling point of tail gas (a mixture of molecular hydrogen and methane) to about 425° C., or to about 370° C., or more typically in a range of from about the normal boiling point of ethane (−89° C.) to about 370° C., or from about the normal boiling point of normal butane (−1° C.) to about 370° C., or from about the normal boiling point of normal pentane (36° C.) to about 370° C. Generally, ≥5 wt. % of the first vapor phase product has a normal boiling point ≥36° C., e.g., ≥10 wt. %, such as ≥25 wt. %, or ≥50 wt. %, or ≥75 wt. %, or ≥90 wt. %, or more; and ≤25 wt. % of the first vapor phase product has a normal boiling point ≥370° C., e.g., ≤15 wt. %, such as ≤10 wt. %, or ≤5 wt. %, or ≤1 wt. %. Those skilled in the art will appreciate, that when the hydrocarbon feed includes a heavy hydrocarbon such as crude oil, the first vapor phase product generally contains substantially all of the feed's naphtha (normal point range of from 10° C. to 200° C.), kerosene (normal boiling point range of from 200° C. to 260° C.), and atmospheric gas oil (normal boiling point range of from 260° C. to 340° C.) fractions, and typically (depending, e.g., on the stringency of the first separation stage's cut point) at least a portion of the feed's light vacuum gas oil fraction (normal boiling point range of 340° C. to 450° C.), e.g., the 410° C. to 450° C. fraction. Typically the first vapor phase product contains ≤5 wt. % of the feed's heavy vacuum gas oil fraction (normal boiling point range of from 450° C. to 570° C.), e.g., ≤1 wt. %. Likewise, the first separation stage is typically configured so that the first liquid phase product has a normal boiling point range ≥340° C., e.g., ≥about 425° C. Typically ≥5 wt. % of the first liquid phase product has a normal boiling point ≥340° C. (or ≥425° C.), e.g., ≥10 wt. %, such as ≥25 wt. %, or ≥50 wt. %, or ≥75 wt. %, or ≥90 wt. %, or more; and ≤25 wt. % of the first vapor product has a normal boiling point ≤340° C., e.g., ≤15 wt. %, such as ≤10 wt. %, or ≤5 wt. %, or ≤1 wt. %. Those skilled in the art will appreciate, that when the hydrocarbon feed includes a heavy hydrocarbon such as crude oil, the first liquid phase product may contain a portion of the feed's light vacuum gas oil, typically ≥1 wt. % of this fraction, or ≥5 wt. %, or ≥10 wt. %, but ≤25 wt. % of this fraction, e.g., ≤10 wt. %, such as ≤5 wt. %); and may also contain a portion of the feed's heavy vacuum gas oil fraction, typically ≥1 wt. %, or ≥10 wt. %, or ≥25 wt. %, but ≤75 wt. % of this fraction, e.g., ≤50 wt. %, such as ≤25 wt. %, or ≤10 wt. %. The first liquid phase product typically contains substantially all of the feed's vacuum resid component (normal boiling point range of from 570° C. to the feed's distillation end point under vacuum distillation conditions), and may also contain a portion of the feed's atmospheric resid component (normal boiling range of from 340° C. to the feed's distillation end point under atmospheric distillation conditions). The term "liquid phase" is not meant to exclude solid phase and vapor phase components that may be present in the liquid phase, e.g., by entrainment. Typically the amounts of such entrained solids and vapors small, e.g., ≤1 wt. %. Likewise, the term "vapor phase" is not meant to exclude solid phase and liquid phase components that may be present in the vapor phase, e.g., by entrainment. Typically the amounts of such entrained solids and liquid (e.g., droplets) small, e.g., ≤1 wt. %.

At least a portion of the first liquid phase is further processed by catalytic cracking. Suitable fluidized catalytic crackers and equipment associated therewith and processes for operating same can include those disclosed in Handbook of Petroleum Refining Processes, 2d Ed., R. A. Meyers, 3.3-3.111, McGraw-Hill, but the invention is not limited thereto. Those skilled in the art will appreciate, that when the first liquid phase product contains at least at least a portion of the feed's atmospheric and vacuum resids and a portion of the hydrocarbon feed's light and heavy vacuum gas oils, then (i) the $C_{4-}$ overhead is typically present in an amount ≤25 wt. %, (ii) the naphtha typically has a normal boiling point boing range of about 3° C. to about 220° C. (generally written as $C_5$ to 430° F.) and is typically present in an amount ≥40 wt. %, (iii) the cycle oil (commonly called light cycle oil) typically has a normal boiling point range of about 220° C. to about 370° C. and is typically present in an amount ≥10 wt. %, and (iv) the bottoms product (commonly referred to as main column bottoms, or "slurry" by virtue of it having a small content of entrained catalyst fines) typically has a normal boiling point range ≤370° C. and is typically present in an amount (hydrocarbon basis, less fines)≤20 wt. %, the weight percents being based on the products of the catalytic cracking (the weight of coke deposited on the catalyst plus the weight of the catalytically cracked effluent. Catalytic cracking conversion (fresh feed basis, e.g., based on the weight of the first liquid phase product) is typically ≥60% wt. %, and more typically ≥70 wt. %.

The catalyst can be or include any one or more catalysts typically used in fluidized catalytic cracking processes. For example, the catalyst can include large-pore molecular sieve catalysts, medium-pore molecular sieve catalysts, or a mixture thereof. Large-pore molecular sieves generally include molecular sieve catalysts having an average pore diameter of about 0.7 nm or greater and are typically used to catalytically "crack" hydrocarbons. The large-pore molecular sieves and the medium-pore molecular sieves can have a crystalline tetrahedral framework oxide component. For example, the crystalline tetrahedral framework oxide component can include zeolites, tectosilicates, tetrahedral aluminophosphates (ALPOs) and tetrahedral silicoaluminophosphates (SAPOs). Conventional catalyst for fluidized catalytic cracking can be used (including a mixture of large pore and shape-selective catalyst), but the invention is not limited thereto.

When the bottoms product is produced by catalytically cracking (e.g., in a fluidized catalytic cracker, "FCC", also commonly referred to as a fluidized catalytic cracking unit, "FCCU") a feed comprising (i) at least a portion of the atmospheric and vacuum resid fractions of the hydrocarbon feed, and (ii) at least a portion of the hydrocarbon feed's atmospheric and vacuum gas oil fractions, the cycle oil typically has a flash point in the range of 50° C. to 100° C., a 50° C. kinematic viscosity in the range of from 2 cSt to 4 cSt, a sulfur content in the range of from 1 wt. % to 5 wt. % and a Cetane Index in the range of from 15 to 40.

The bottoms product typically has an API gravity in the range of from −6° to +8°, a sulfur content in the range of 0.3 wt. % to 5.0 wt. %, a nitrogen content in the range of from about 0.1 wt. % to about 0.5 wt. %, and a solids content of about 1000-6000 ppmw, the weight percents being based on the weight of the bottoms product. It is generally desirable to decrease the solids content of the bottoms product before hydroprocessing. Conventional methods can be used to do so, but the invention is not limited thereto. Suitable methods (and additional properties of the bottoms product, particularly bottoms products resulting from catalytically cracking a first liquid phase product comprising resid) are disclosed in V. Salco, The Cure to Separation Anxiety, Hydrocarbon Engineering, 83-86, March 2017.

The bottoms product or the fluxed bottoms can be subjected to hydroprocessing conditions to produce the hydroprocessed product. Hydroprocessing the bottoms product or the fluxed bottoms can be carried out under hydroconversion conditions, e.g., under conditions for carrying out one or more of pretreatment, hydrocracking (including selective hydrocracking), hydrogenation, hydrotreating, hydrodesulfurization, hydrodenitrogenation, hydrodemetallation, hydrodearomatization, hydroisomerization, or hydrodewaxing of the bottoms product or the fluxed bottoms. In some examples, the bottoms product or the fluxed bottoms can be hydroprocessed in one or more hydroprocessing units that can include one or more hydroprocessing vessels or zones. The hydroprocessing vessel or zone can include one or more catalysts disposed therein. The catalyst can be in the form of a fixed catalyst bed, a circulating or slurry bed, or any other configuration. In some examples, the bottoms product or the fluxed bottoms, prior to being subjected to hydroprocessing can be subjected to a deasphalting process to produce a deasphalted bottoms product or a deasphalted fluxed bottoms and the deasphalted bottoms product or the deasphalted fluxed bottoms can be hydroprocessed.

In particular aspects, the pre-treater hydroprocessing conditions can include one or more of $T_{PT} \geq 150°$ C., e.g., $\geq 200°$ C. but less than $T_{BP}$ (e.g., $T_{PT} \leq T_{BP}-10°$ C., such as $T_{PT} \leq T_{BP}-25°$ C., such as $T_{PT} \leq T_{BP}-50°$ C.), a total pressure $P_{PT}$ that is $\geq 8$ MPa but less than $P_{BP}$, $WHSV_{PT} \geq 0.2$ hr$^{-1}$, $\geq 0.25$ hr$^{-1}$, or $\geq 0.3$ hr$^{-1}$ and greater than $WHSV_{BP}$ (e.g., $WHSV_{PT} > WHSV_{BP}+0.01$ hr$^{-1}$, such as $\geq WHSV_{BP}+0.05$ hr$^{-1}$, or $\geq WHSV_{BP}+0.1$ hr$^{-1}$, or $\geq WHSV_{BP}+0.5$ hr$^{-1}$, or $\geq WHSV_{BP}+1$ hr$^{-1}$, or $\geq WHSV_{BP}+10$ hr$^{-1}$, or more), and a molecular hydrogen consumption rate in the range of from 150 standard cubic meters of molecular hydrogen per cubic meter of the bottoms product or the bottoms product in the fluxed bottoms (S m$^3$/m$^3$) to about 400 standard cubic meters of molecular hydrogen per cubic meter of the bottoms product or bottoms product in the fluxed bottoms (S m$^3$/m$^3$) (845 SCF/B to 2250 SCF/B) but less than that of bottoms product hydroprocessing.

The pretreatment hydroprocessing conditions typically include $T_{PT}$ in the range of from 260° C. to 300° C.; $WHSV_{PT}$ in the range of from 1.5 hr$^{-1}$ to 3.5 hr$^{-1}$, e.g., 2 hr$^{-1}$ to 3 hr$^{-1}$; a $P_{PT}$ in the range of from 6 MPa to 13.1 MPa; and a molecular hydrogen consumption rate in the range of from 100 standard cubic feet per barrel of the bottoms product or the bottoms product in the fluxed bottoms (SCF/B) (18 S m$^3$/m$^3$) to 600 standard cubic feet per barrel of the bottoms product or the bottoms product in the fluxed bottoms (SCF/B) (107 S m$^3$/m$^3$). Although the amount of molecular hydrogen supplied to a hydroprocessing stage operating under pretreatment hydroprocessing conditions is generally selected to achieve the desired molecular hydrogen partial pressure, it is typically in a range of about 300 standard cubic feet per barrel of bottoms product or fluxed bottoms (SCF/B) (53 S m$^3$/m$^3$) to about 1000 standard cubic feet per barrel of bottoms product or fluxed bottoms (SCF/B) (178 S m$^3$/m$^3$). Optionally, one or more stages for solids-removal and/or guard-bed hydroprocessing are carried out upstream of the pre-treater, as disclosed in U.S. Patent Application No. 62/716,754.

The molecular hydrogen can be combined with the bottoms product or the fluxed bottoms upstream of the hydroprocessing unit and/or introduced directly to the hydroprocessing unit. The molecular hydrogen can be relatively pure hydrogen or can be in the form of a "treat gas" that contains sufficient molecular hydrogen for use in the pre-treater hydroprocessing and optionally includes other gases (e.g., nitrogen and light hydrocarbons such as methane) that generally do not adversely interfere with or affect either the reactions or the products. In some examples, the treat gas can include $\geq 50$ vol % of molecular hydrogen, $\geq 75$ vol % of molecular hydrogen, or $\geq 90$ vol % of molecular hydrogen.

The hydroprocessing of the bottoms product or the fluxed bottoms under the pre-treater hydroprocessing conditions can be carried out in the presence of a catalytically-effective amount of at least one catalyst having activity for hydrocarbon hydroprocessing. Illustrative catalysts can include, but are not limited to, conventional hydroprocessing catalysts such as those used in resid and/or heavy oil hydroprocessing. Illustrative catalysts can include, but are not limited to, bulk metallic catalysts and/or supported catalysts. The metals can be in elemental form or in the form of a compound. In some examples, the catalyst can be or include at least one metal from any of Groups 5 to 10 of the Periodic Table of the Elements (tabulated as the Periodic Chart of the Elements, The Merck Index, Merck & Co., Inc., 1996). Examples of such metals include, but are not limited to, copper, vanadium, chromium, molybdenum, tungsten, manganese, technetium, rhenium, iron, cobalt, nickel, ruthenium, palladium, rhodium, osmium, iridium, platinum, or mixtures thereof. Suitable conventional catalysts include one or more of RT-621, which is described as a resid conversion catalyst in Advances of Chemical Engineering 14, table XXIII, Academic Press, 1989; KF860 available from Albemarle Catalysts Company LP, Houston Tex.; NEBULA® Catalyst, such as NEBULA® 20, available from the same source; CENTERA® catalyst, available from Criterion Catalysts and Technologies, Houston Tex., such as one or more of DC-2618, DN-2630, DC-2635, and DN-3636; ASCENT® Catalyst, available from the same source, such as one or more of DC-2532, DC-2534, and DN-3531; and FCC pre-treat catalyst, such as DN3651 and/or DN3551, available from the same source.

In some examples, the catalyst can include a total amount of Groups 5 to 10 metals per gram of catalyst of $\geq 0.0001$ grams, $\geq 0.001$ grams, or $\geq 0.01$ grams, where the grams are calculated on an elemental basis. For example, the catalyst can include a total amount of Group 5 to 10 metals of about 0.0001 grams, about 0.001 grams, or about 0.05 grams to about 0.08 grams, about 0.1 grams, about 0.3 grams, or about 0.6 grams. In some examples, the catalyst can also include, in addition to at least one metal from any of Groups 5 to 10, at least one Group 15 element. An example of a Group 15 element is phosphorus. When a Group 15 element is utilized, the catalyst can include a total amount of elements of Group 15 of about 0.000001 grams, about 0.00001 grams, about 0.00005 grams, or about 0.0001 grams to about 0.001 grams, about 0.03 grams, about 0.06 grams, or about 0.1 grams, where the grams are calculated on an elemental basis.

The bottoms product of the fluxed bottoms can primarily be in the liquid phase when subjected to the pre-treater hydroprocessing conditions. For example, $\geq 75$ wt. % of the bottoms product or the fluxed bottoms, $\geq 80$ wt. % of the bottoms product or the fluxed bottoms, $\geq 90$ wt. % of the bottoms product or the fluxed bottoms, or $\geq 99$ wt. % of the bottoms product or the fluxed bottoms can be in the liquid phase when subjected to the pre-treater hydroprocessing conditions. The pre-treater hydroprocessing conditions can produce a pretreated bottoms or a pre-treated fluxed bottom that can include (i) a vapor portion that can include unreacted treat gas, primarily vapor products derived from the treat gas and the bottoms product and (ii) a liquid portion that can include unreacted bottoms product and other products, e.g., cracked products derived from the bottoms product that can be produced during the pre-treater hydroprocessing conditions.

In some examples, the liquid portion and the vapor portion in the pre-treated bottoms product or the pre-treated fluxed bottoms can be separated. The vapor portion can be upgraded to remove impurities, e.g., sulfur compounds and/or light paraffinic hydrocarbon, and the upgraded vapor can be re-cycled as a treat gas for use in hydroprocessing the bottoms product or the fluxed bottoms, for example. The liquid portion can be hydroprocessed under the bottoms product hydroprocessing conditions to produce the hydroprocessed product. In other examples, the pre-treated bottoms product or the pre-treated fluxed bottoms, i.e., both the vapor portion and liquid portion, can be hydroprocessed under the bottoms product hydroprocessing conditions to produce the hydroprocessed product. In some examples, prior to subjecting the pre-treated bottoms product or pre-treated fluxed bottoms or the liquid portion separated therefrom to the bottoms product hydroprocessing conditions, the pre-treated bottoms product or the pre-treated fluxed bottoms or the liquid portion separated therefrom can be processed, e.g., subjected to additional solids removal processes.

The bottoms product hydroprocessing conditions can be carried out in at least one hydroprocessing zone located in at least one bottoms product hydroprocessing stage of a bottoms product hydroprocessor reactor. In some examples, the bottoms product hydroprocessor reactor can be in the form of a conventional hydroprocessing reactor. The catalyst(s) and amount(s) thereof can be selected from among the same catalysts amounts specified for use in the pre-treater hydroprocessing conditions.

The bottoms product hydroprocessing conditions can include one or more of (a) a temperature ($T_{BP}$) of ≥200° C. to about 500° C., (b) a weight hour space velocity ($WHSV_{BP}$) of ≥0.2 hr$^{-1}$, ≥0.25 hr$^{-1}$, or ≥0.3 hr$^{-1}$ to about 20 hr$^{-1}$ based on a weight of the pre-treated bottoms product or the pre-treated fluxed mixture, (c) a total pressure ($P_{BP}$) of ≥6 MPa or ≥8 MPa to about 14 MPa, and (d) in the presence of molecular hydrogen supplied at a rate ($SR_{BP}$) of about 150 to about 1,780, e.g., ≥534, standard cubic meters per cubic meter of the pre-treated bottoms product or the pre-treated fluxed bottoms. In some examples, the bottoms product hydroprocessing conditions can include one or more of (a) a $T_{BP}$ of about 250° C., about 275° C., about 300° C., about 350° C., about 360° C., or about 375° C. to about 390° C., about 400° C., about 410° C., about 425° C., about 450° C., about 475° C., or about 500° C., (b) a $WHSV_{BP}$ of about 0.5 hr$^{-1}$, about 0.7 hr$^{-1}$, about 0.9 hr$^{-1}$, about 1 hr$^{-1}$, 1.2 hr$^{-1}$, or about 1.5 hr$^{-1}$ to about 5 hr$^{-1}$, about 10 hr$^{-1}$, about 15 hr$^{-1}$, or about 20 hr$^{-1}$, (c) a $SR_2$ of about 534, about 550, about 575, about 600, or about 650 standard cubic meters per cubic meter of the pre-treated bottoms product or the pre-treated fluxed bottoms to about 700, about 800, about 900, about 1,000, about 1,250, about 1,500 or about 1,750 standard cubic meters per cubic meter of the pre-treated bottoms product or the pre-treated fluxed bottoms, and (d) a PT of ≥6 MPa or ≥8 MPa to about 10 MPa, about 12 MPa, or about 13.1 MPa. In the bottoms product hydroprocessing conditions the molecular hydrogen can be consumed at a rate of about 62, about 80, about 100, about 125, about 150, about 250, about 285, or about 300 standard cubic meters per cubic meter of the bottoms product in the pre-treated bottoms product or the bottoms product in the pre-treated fluxed bottoms to about 500, about 550, about 570, about 600, or about 625 standard cubic meters per cubic meter of the bottoms product in the pre-treated bottoms product or the bottoms product in the pre-treated fluxed bottoms. In some examples, the bottoms product hydroprocessing conditions can also include a molecular hydrogen partial pressure during the tar hydroprocessing of ≥2.75 MPa, ≥3.5 MPa, ≥5 MPa, ≥6 MPa, ≥8 MPa, or ≥11 MPa to about 14 MPa or less, about 13 MPa or less, or about 12 MPa or less. In some examples, the molecular hydrogen partial pressure during the tar hydroprocessing conditions can be about 14 MPa or less, about 13 MPa or less, or about 12 MPa or less.

The molecular hydrogen can be combined with the pre-treated bottoms product of the pre-treated fluxed bottoms or the liquid portion separated therefrom upstream of the bottoms product hydroprocessor and/or introduced directly to the bottoms product hydroprocessor. In other examples, the molecular hydrogen can be cascaded from the pre-treater hydroprocessor with the pre-treated product to the bottoms product hydroprocessor. The molecular hydrogen can be relatively pure hydrogen or can be in the form of a "treat gas" that contains sufficient molecular hydrogen for use in the pre-treater hydroprocessing and optionally includes other gases (e.g., nitrogen and light hydrocarbons such as methane) that generally do not adversely interfere with or affect either the reactions or the products. In some examples, the treat gas can include ≥50 vol % of molecular hydrogen, ≥75 vol % of molecular hydrogen, or ≥90 vol % of molecular hydrogen.

In some examples, at least the hydroprocessor heavy product and the utility fluid product can be separated from the hydroprocessed product. In other examples, the hydroprocessor heavy product, the utility fluid product, and an overhead can be separated from the hydroprocessed product. In some examples, the hydroprocessor heavy product can be further processed, e.g., subjected to additional hydroprocessing, to adjust or otherwise modify one or more properties thereof. The second liquid phase product, the hydroprocessed product, and the hydroprocessor heavy product are themselves valuable products, and can be used, e.g., as a relatively high-sulfur fuel oil (high sulfur in comparison with the first and second fuel oil products) or as a blending component thereof. Non-limiting examples of blendstocks suitable for blending with one or more of second liquid phase product, the hydroprocessed product and the hydroprocessor heavy product include one or more of bunker fuel; burner oil; heavy fuel oil, e.g., No. 5 and No. 6 fuel oil; high-sulfur fuel oil; low-sulfur fuel oil; regular-sulfur fuel oil (RSFO); gas oil as may be obtained from the distillation of crude oil, crude oil components, and hydrocarbon derived from crude oil (e.g., coker gas oil), and the like. For example, the second liquid phase product can be used as a blending component to produce a fuel oil composition comprising <0.5 wt. % sulfur. Although the second liquid phase product and the hydroprocessor heavy product are improved products over the bottoms product and/or the tar product, and are useful as fuel or blendstock "as-is", it is typically beneficial to carry out further processing.

The hydroprocessor heavy product has desirable properties, e.g., a 15° C. density that is typically ≥0.10 g/cm$^3$ less than the density of the tar product. For example, the hydroprocessor heavy product can have a density that is ≥0.12, or ≥0.14, or ≥0.15, or ≥0.17 g/cm$^3$ less than the density of the tar product. The hydroprocessor heavy product's 50° C. kinematic viscosity is typically ≤1000 cSt. For example, the viscosity of the hydroprocessor heavy product can be ≤500 cSt, e.g., ≤150 cSt, such as ≤100 cSt, or ≤75 cSt, or ≤50 cSt, or ≤40 cSt, or ≤30 cSt. Generally, the tar hydroprocessing results in a significant viscosity improvement over the pretreated tar. For example, when the 50° C. kinematic viscosity of the tar product (e.g., obtained as feed from a tar knock-out drum) is ≥1.0×10$^4$ cSt, e.g., ≥1.0×10$^5$ cSt, ≥1.0×10$^6$ cSt, or ≥1.0×10$^7$ cSt, the 50° C. kinematic viscosity of the hydroprocessor heavy product is typically ≤200 cSt, e.g., ≤150 cSt, such as ≤100 cSt, or ≤75 cSt, or ≤50 cSt, or ≤40 cSt, or ≤30 cSt. Particularly when the tar product has a sulfur content ≥1 wt. %, upstream of the pre-treater hydroprocessor, the hydroprocessor heavy product typically has a sulfur content ≥0.5 wt. %, e.g., in a range of about 0.5 wt. % to about 0.8 wt. %. In some examples, the hydroprocessor heavy product can have a sulfur content of <0.5 wt. %, such as about 0.05 wt. % to about 0.4 wt. %. In some examples, the hydroprocessor heavy product can have a density of <0.99 g/cm$^3$, a cetane value of ≥20, a CCAI of <870, a sulfur content of <0.5 wt. %, and a sediment content of <0.1 wt. %.

In some examples, the hydroprocessor heavy product can be further processed, e.g., subjected to additional hydroprocessing, to adjust or otherwise modify one or more properties thereof. The additional hydroprocessing (not shown in the figures) can be carried out under conditions (re-treater hydroprocessing conditions) that are typically more severe than those of the pre-treater (itself a hydroprocessor) or the bottoms product hydroprocessor. Aromatic content of the utility fluid is not affected by the additional hydroprocessing because the utility fluid is recovered before the additional hydroprocessing. The utility fluid is not needed during the re-treater hydroprocessing because, e.g., the bottoms product hydroprocessor and optionally the pre-treater hydroprocessor sufficiently decrease the content of foulant precursors in the feed to the additional hydroprocessor. The product of such additional hydroprocessing can be the first fuel oil and/or a blending component thereof. The hydroprocessor heavy product and the utility fluid product can be separated from the hydroprocessed product according to the processes and systems disclosed in U.S. Pat. Nos. 9,090,836; 9,637,694; 9,777,227; and International Patent Application Publication No. WO 2018/111574.

Typically, the additional hydroprocessing is carried out under re-treater hydroprocessing conditions in at least one hydroprocessing zone located in at least one re-treater hydroprocessing stage of a re-treater hydroprocessor reactor with little or no utility fluid. The re-treatment hydroprocessing conditions, which are typically more severe than the tar hydroprocessing conditions, can include a temperature $(T_R) \geq 360°$ C.; a space velocity (WHSV$_R$)≤0.6 hr$^{-1}$, based on the weight of the hydroprocessor heavy product that is subjected to the retreatment; a molecular hydrogen supply rate ≥2500 standard cubic feet per barrel of hydroprocessed tar (SCF/B) (445 S m$^3$/m$^3$); a total pressure ("P$_R$")≥3.5 MPa, e.g., ≥6 MPa; and WHSV$_R$<WHSV$_{BP}$. The retreatment hydroprocessing conditions typically include $T_R \geq 370°$ C.; e.g., in the range of from 370° C. to 415° C.; WHSV$_R$≤0.5 hr$^{-1}$, e.g., in the range of from 0.2 hr$^{-1}$ to 0.5 hr$^{-1}$; a molecular hydrogen supply rate ≥3000 SCF/B, e.g., in the range of from 3000 SCF/B (534 S m$^3$/m$^3$) to 6000 SCF/B (1068 S m$^3$/m$^3$); and a total pressure ("P$_R$")≥6 MPa, e.g., in the range of from 6 MPa to 13.1 MPa. Optionally, $T_R > T_{BP}$ and/or WHSV$_R$<WHSV$_{BP}$. One product of the additional hydroprocessing is heavy hydrocarbon comprising re-treated tar.

The re-treated hydroprocessor heavy product typically has a sulfur content ≤0.3 wt. %, e.g., ≤0.2 wt. %. Other properties of the re-treated hydroprocessor heavy product can include a hydrogen:carbon molar ratio ≥1.0, e.g., ≥1.05, such as ≥1.10, or ≥1.055; an S$_{BN}$≥185, such as ≥190, or ≥195; an I$_N$≤105, e.g., ≤100, such as ≤95; a 15° C. density ≤1.1 g/cm$^3$, e.g., ≤1.09 g/cm$^3$, such as ≤1.08 g/cm$^3$, or ≤1.07 g/cm$^3$; a flash point ≥, or ≤−35° C. Generally, the re-treated tar oil has 50° C. kinematic viscosity that is less than that of the hydroprocessor heavy product, and is typically ≤1000 cSt, e.g., ≤900 cSt, such as ≤800 cSt. The retreating generally results in a significant improvement in in one or more of viscosity, solvent blend number, insolubility number, and density over that of the hydroprocessor heavy product fed to the retreater. Desirably, since the retreating can be carried out without utility fluid, these benefits can be obtained without utility fluid hydrogenation or cracking.

The re-treated hydroprocessor heavy product can be utilized as a fuel and/or blended with one or more blendstocks, e.g., to produce a lubricant or fuel, e.g., a transportation fuel. Suitable blendstocks include those specified for blending with the second liquid phase product, the first hydroprocessed product and the hydroprocessor heavy product. Selected conditions for the pre-treater, the tar hydroprocessor, and the re-treater, and the properties of certain products and by-products are disclosed in WO Publication No. WO2018/111574.

As noted above, in some examples, the tar product can be mixed, blended, combined, or otherwise contacted with the bottoms product and/or the fluxed bottoms to produce a bottoms product-tar mixture or a fluxed bottoms-tar mixture that can also be hydroprocessed under the bottoms product hydroprocessing conditions and optionally the pre-treater hydroprocessing conditions to produce the hydroprocessed product. In some examples, the bottoms product, the fluxed bottoms, the bottoms product-tar mixture, the fluxed bottoms-tar mixture, fluxed bottoms, or a fluxed bottoms-tar-utility fluid mixture can be hydroprocessed according to the processes and systems disclosed in U.S. Pat. Nos. 9,090,836; 9,637,694; 9,777,227; and International Patent Application Publication No. WO 2018/111574.

The vapor phase product (in certain aspects, the first vapor phase product) can be subjected to steam cracking conditions sufficient to produce the steam cracker effluent. Illustrative steam cracking conditions can include, but are not limited to, one or more of: exposing the vapor phase product to a temperature (as measured at a radiant outlet of a steam cracking apparatus) of at least 400° C., e.g., a temperature of about 700° C. to about 900° C., a pressure of about 0.1 bar to about 5 bars (absolute), and/or a steam cracking residence time of about 0.01 seconds to about 5 seconds. In some examples, the vapor phase can be introduced to a radiant section of a steam cracking furnace to produce the steam cracker effluent. In some examples, the vapor phase product can be steam cracked according to the processes discussed and described in U.S. Pat. Nos. 6,419,885; 7,993,435; 9,637,694; and 9, 777,227; and International Patent Application Publication No. WO 2018/111574.

Steam cracker effluent from the steam cracking furnace's radiant section is typically cooled (e.g., indirectly in one or more TLEs) and/or quenched, e.g., by contacting the steam cracker effluent with at least one quench fluid at one or more locations downstream of the radiant section. The steam cracker effluent can be directly contacted with the quench fluid that can be or can include the utility fluid product to produce the cooled steam cracker effluent. In some examples, the steam cracker effluent can also be cooled by indirect heat exchange with a quench medium, e.g., liquid water or steam, before, during, and/or after the steam cracker effluent is directly contacted with the quench fluid. For example, the steam cracker effluent can be cooled by indirect heat exchange, e.g., via one or more transfer line exchangers, with steam to produce superheated steam and a pre-cooled steam cracker effluent. The quench fluid that can be or can include the utility fluid product can be directly contacted with the pre-cooled steam cracker effluent to produce the cooled steam cracker effluent.

In some examples, a plurality of products can be separated from the cooled steam cracker effluent. In some examples, the tar product and the upgraded steam cracker effluent can be separated from the cooled steam cracker effluent. In these and other examples, at least a process gas is separated from the upgraded steam cracker effluent, where the process gas typically includes at least one of a tail gas, ethane, propane, ethylene, propylene, benzene, crude $C_4$ hydrocarbons, steam cracker naphtha. Alternatively or in addition, streams such as SCN and/or SCGO are separated from the cooled steam cracker effluent. In some examples, a mogas blendstock can be produced. Motor gasoline ("Mogas") blendstock is a mixture that includes $C_4$-$C_{12}$ hydrocarbons having an initial normal boiling point of about 35° C. and a final boiling point of about 200° C. The mogas blendstock can include a stabilized steam cracker naphtha produced by hydroprocessing the steam cracker naphtha in the presence of molecular hydrogen and a catalyst. The tail gas can include, but is not limited to, molecular hydrogen, methane, or a mixture thereof. In some examples, the tar product and at least two, at least three, at least four, at least five, at least six, at least seven, or all of molecular hydrogen, ethane, ethylene, propane, propylene, crude $C_4$ hydrocarbons, SCN, and SCGO can be separated from the cooled steam cracker effluent.

Conventional equipment and methods can be used in separating at least the tar product and other products, e.g., the upgraded steam cracker effluent, from the cooled steam cracker effluent, but the invention is not limited thereto. For example, one or more flash drums, knock out drums, etc., can be used. Likewise, Conventional equipment and methods can be used in separating at least a process gas from the upgraded steam cracker effluent, but the invention is not limited thereto. For example, the process gas and other streams, e.g., water (such as recovered dilution steam and/or water condensed from dilution steam), SCN, SCGO, etc, can be separated from the upgraded steam cracker effluent using one or more of fractionators, water-quench towers, indirect condensers, etc. In some examples, illustrative separation stages can include those disclosed in U.S. Pat. No. 8,083, 931, for example. In other examples, the products that can be separated from the cooled steam cracker effluent or constituents thereof, e.g., the tar product, upgraded steam cracker effluent, process gas, ethylene, and propylene, etc. can be separated according to the processes and systems disclosed in U.S. Patent Application Publication No. 2014/ 0357923.

Although the tar product is typically separated from the cooled steam cracker effluent itself, at least of portion of the tar product can be obtained from one or more streams other that have been separated from the cooled steam cracker effluent, e.g., from the upgraded steam cracker effluent. For example, the tar product can be separated from a steam cracker gas oil stream and/or a bottoms stream of the steam cracker's primary fractionator, from flash-drum bottoms (e.g., the bottoms of one or more tar knock out drums located downstream of the pyrolysis furnace and upstream of the primary fractionator), or a combination thereof. In some examples, the tar product can be or include a mixture of primary fractionator bottoms and tar knock-out drum bottoms. In other examples the tar product consists essentially of or even consists of tar knock-out drum bottoms.

The tar product can be or include, but is not limited to, a mixture of hydrocarbons having one or more aromatic components and, optionally, non-aromatic and/or non-hydrocarbon molecules, the mixture being derived from hydrocarbon pyrolysis, with at least 70% to about 100% of the mixture having a boiling point at atmospheric pressure that is at least 290° C., e.g., 290° C. to about 500° C. In some examples, the tar product can have an initial boiling point of at least 200° C. In other examples, at least 90 wt. % to about 100 wt. % of the tar product can have a boiling point at atmospheric pressure at least 290° C., e.g., 290° C. to about 500° C. In other examples, the tar product can include at least 50 wt. %, at least 75 wt. %, or at least 90 wt. % to about 97 wt. %, about 99 wt. %, or about 100 wt. % of hydrocarbon molecules (including mixtures and aggregates thereof), based on the weight of the tar product, and (i) one or more aromatic components and (ii) a number of carbon atoms of at least 15, e.g., 15 to about 100. In some examples, the tar product can have a metals content of about 100 ppmw to about 2,000 ppmw, e.g., about 1,000 ppmw or less, based on the weight of the tar product. In some examples, the tar product can be what is also sometimes referred to as pyrolysis tar obtained from steam cracking.

The tar product can also include tar heavies. "Tar heavies" are a product of hydrocarbon pyrolysis having an atmospheric boiling point of at least 565° C. and can include at least 5 wt. %, e.g., 5 wt. % to about 20 wt. %, about 50 wt. %, about 75 wt. %, or about 100 wt. %, of molecules having a plurality of aromatic cores based on the weight of the product. The tar heavies are typically solid at 25° C. and generally include the fraction of the tar product that is not soluble in a 5:1 (vol:vol) ratio of n-pentane:tar product at 25° C. Tar heavies can also include asphaltenes and other high molecular weight molecules.

In some examples, the tar product can include about 5 wt. % to about 40 wt. % of tar heavies, based on the weight of the tar product, can have an °API gravity measured at a temperature of 15.8° C. of 8.5 or less, e.g., about 1 to about 8.5, as measured according to ASTM D287-12b, and can have a 50° C. viscosity of about 200 cSt to about 10,000,000 cSt, as measured according to ASTM D445-17a. In some examples, the tar product can also have a sulfur content of about 0.5 wt. %, about 1 wt. %, about 1.5 wt. %, or about 2 wt. % to about 4 wt. %, about 5 wt. %, about 6 wt. %, or about 7 wt. %, based on the weight of the tar product. In other examples, the tar product can include less than 0.5 wt. %, less than 0.3 wt. %, less than 0.1 wt. %, or less than 0.05 wt. % of sulfur, based on the weight of the tar product.

In some examples, the tar product can include about 5 wt. % to 40 wt. % of tar heavies, based on the weight of the tar product, can have a density at 15° C. of about 1.01 g/cm3 to about 1.19 g/cm3, and can have a 50° C. viscosity of at least 200 cSt to about 10,000,000 cSt. In some examples, the tar product can have a 50° C. kinematic viscosity of at least 10,000 cSt, or at least 100,000 cSt, to about 1,000,000 cSt, or about 10,000,000 cSt or more. Optionally, the tar product can have an IN greater than 80 and greater than 70 wt. % of the tar product's molecules can have an atmospheric boiling point of at least 290° C. Typically, the tar product can have an insoluble content of at least 0.5 wt. %, at least 1 wt. %, at least 2 wt. %, at least 4 wt. %, or at least 5 wt. % to about 6 wt. %, about 8 wt. %, or about 10 wt. % or more. The insolubles content refers to the amount (in wt. %) of components of a hydrocarbon-containing composition that are insoluble in a mixture of 25% by volume heptane and 75% by volume toluene. Determination of the insolubles content is well-known and can determined according to the procedure disclosed in International Patent Application Publication No. WO 2018/111574.

Certain embodiments and features have been described using a set of numerical upper limits and a set of numerical lower limits. It should be appreciated that ranges including the combination of any two values, e.g., the combination of any lower value with any upper value, the combination of any two lower values, and/or the combination of any two upper values are contemplated unless otherwise indicated. Certain lower limits, upper limits and ranges appear in one or more claims below. All numerical values are "about" or "approximately" the indicated value, and take into account experimental error and variations that would be expected by a person having ordinary skill in the art.

Various terms have been defined above. To the extent a term used in a claim is not defined above, it should be given the broadest definition persons in the pertinent art have given that term as reflected in at least one printed publication or issued patent. Furthermore, all patents, patent application publications, test procedures, and other documents cited in this application are fully incorporated by reference herein to the extent such disclosure is not inconsistent with this application and for all jurisdictions in which such incorporation is permitted.

Certain aspects of the invention which relate to the recovery of certain unsaturated hydrocarbon including aromatic hydrocarbon will now be described in more detail. The invention is not limited to these aspects, and this description should not be interpreted as foreclosing other aspects within the broader scope of the invention.

Figure 3:
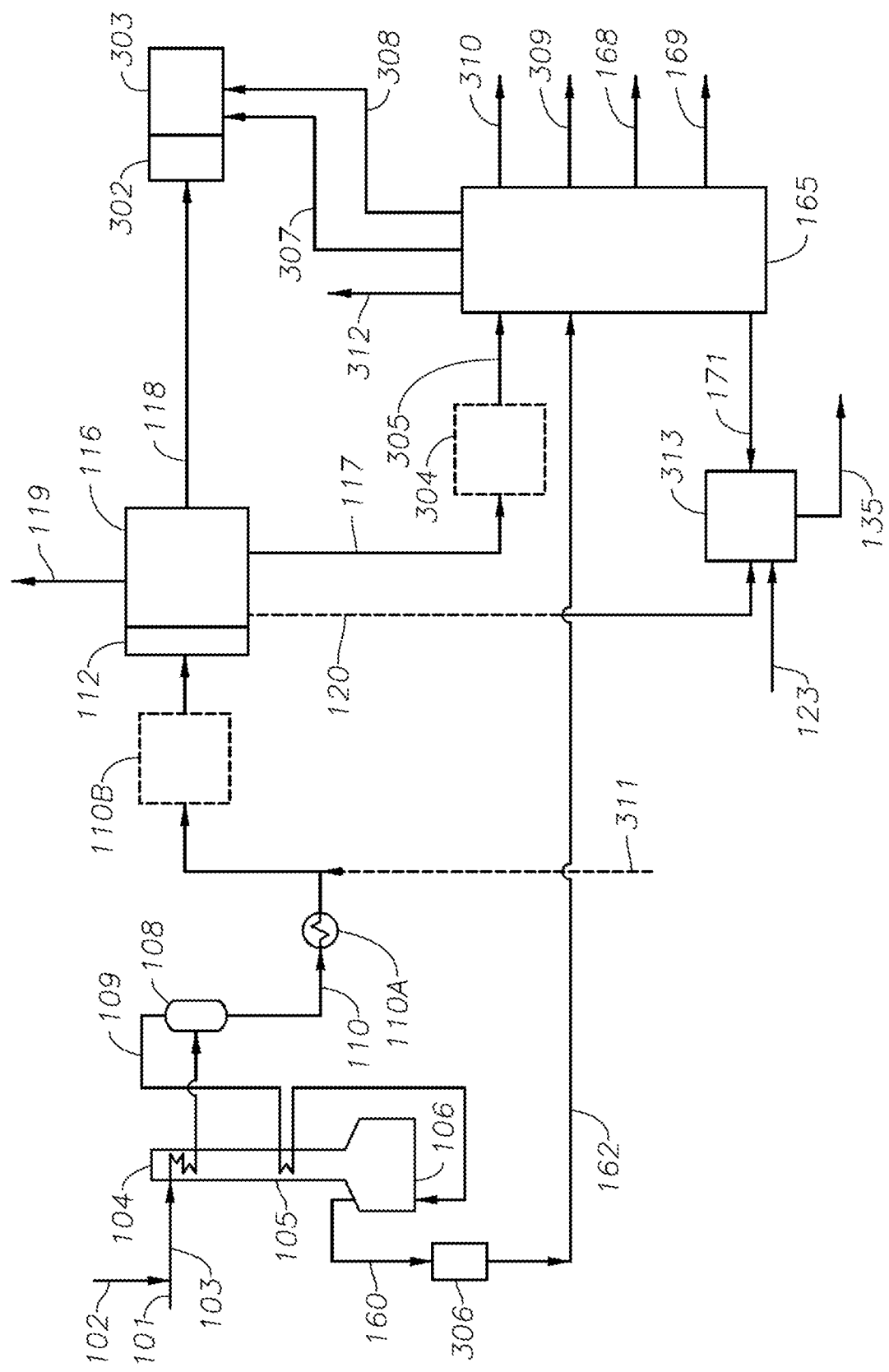
FIG. 3 schematically shows certain aspects which include optional stages for naphtha hydroprocessing, reforming, and aromatics production.

Referring now to FIG. 3, a hydrocarbon feed is introduced into line 101, and combined with steam via line 102. The hydrocarbon-steam mixture is conducted to convection section 105 of steam cracking furnace 104 for heating. A heated mixture is conducted to vapor-liquid separator 108 that is integrated with the steam cracking furnace as shown. The first vapor phase product is returned to the convection section for heating via line 109. The heated first vapor phase product conducted through the radiant section 106 of the furnace for pyrolysis, and the steam cracking effluent is conducted away from the furnace via line 160. The steam cracking effluent is cooled in stage 306, which can include indirect cooling (e.g., using one or more TLEs) and/or direct cooling by contact with quench fluid. The first liquid phase product of line 110 can be optionally cooled or heated in heat transfer stage 110A, and can be optionally pretreated in upgrading stage 110B, e.g., for hydroprocessing, as indicated in the description of those aspects illustrated by FIG. 1. Those skilled in the art will appreciate that it can be desirable to carry out the upgrading when the cut point for separator 108 is >400° C., e.g., in a range of from >400° C. to 550° C., such as from 405° C. to 450° C., or 410° C. to 425° C. The first liquid phase product and/or upgraded first liquid phase product is conducted to riser reactor 112, which is typically a fluidized catalytic cracking unit, e.g., a high-severity fluid catalytic cracking unit, such as those described in U.S. Patent Application Publication No. 2018-0057758 and in more detail in the Meyers reference. Separation stage 116 can be used to separate and recover from the catalytically cracked effluent one or more of the light hydrocarbon product via line 117, the naphtha via line 118, the cycle oil via line 119, and the bottoms product via line 120. The naphtha is typically further processed in hydroprocessor 302. Conventional naphtha hydroprocessing can be used, e.g., conventional selective and/or non-selective naphtha catalytic hydroprocessing, but the invention is not limited thereto. A reformer 303 can be used to produce reformate from the hydroprocessed naphtha. Conventional catalytic reformers (e.g., CCR) can be used, but the invention is not limited thereto. Alkylation, e.g., conventional alkylation, can be used to produce aromatics such as benzene, toluene, ethylbenzene, and xylene from the reformate.

Cooled steam cracker effluent 162 and the light hydrocarbon product 117 can be conducted to separation stage 165 for recovery of certain products of steam cracking and/or FCC, e.g., the tar product-diluent mixture 171, gas oil 169, naphtha 168, $C_4$ hydrocarbon 309, ethylene and/or propylene 310, benzene 308, toluene 307, and tail gas 312. The tar product-diluent mixture 166 can be conducted to hydroprocessing stage 313, which generally includes at least hydroprocessor 130 and also typically hydroprocessor 125 for pretreating the tar product-diluent mixture upstream of hydroprocessor 130 as shown in FIG. 1. These hydroprocessing stages can be operated under substantially the same conditions (temperature, pressure, etc.) as those indicated for the aspects illustrated by FIG. 1. Molecular hydrogen is provided via line 123. The hydroprocessed product is conducted away via line 135.

Although it is not required, a pretreatment stage 304 can be used upstream of stage 165 to remove from the light hydrocarbon product at least a portion of one or more of molecular hydrogen, methane, ammonia, carbon dioxide, arsine, mercury, hydrogen sulfide, carbonyl sulfide, mercaptans, and carbon disulfide, oxygenates and water. The pretreatment can be particularly beneficial when the hydrocarbon feed of line 101 comprises a heavy crude oil, e.g., one having an API gravity in the range of from 5° to 20°. Conventional light hydrocarbon pretreatment technology can be used, but the invention is not limited thereto. Pretreated light hydrocarbon product can be conducted to stage 165 via line 305.

Figure 5:
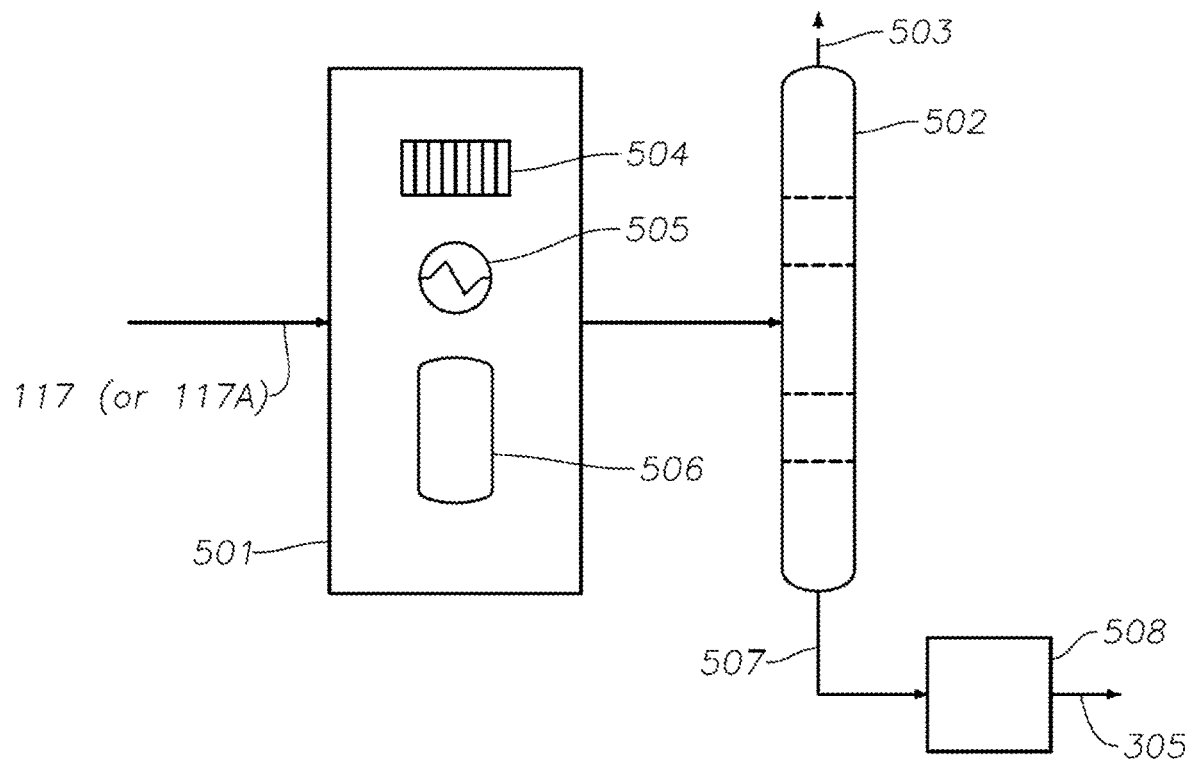
FIG. 5 schematically shows a representative cryogenic demethanizer that is suitable for use in one or more aspects.
Figure 6:
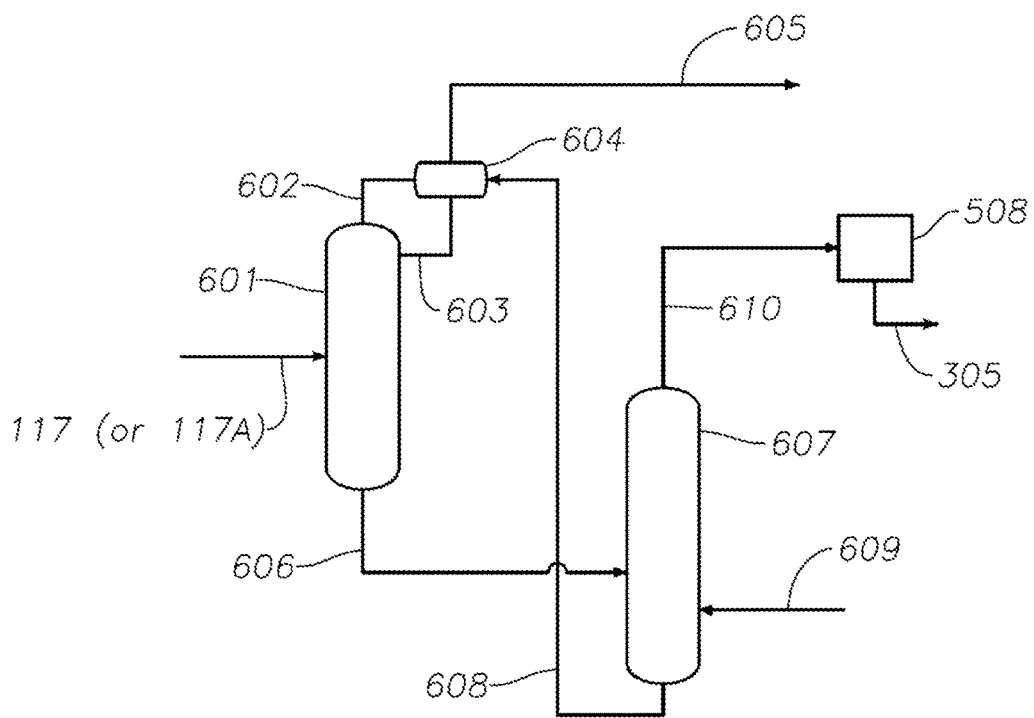
FIG. 6 schematically shows a representative cryogenic demethanizer that is suitable for use in one or more aspects.

In certain aspects, pretreatment stage 304 includes at least one demethanizer, e.g., a cryogenic demethanizer (FIG. 5) and/or an absorption demethanizer (FIG. 6). Conventional demethanizers can be used, but the invention is not limited thereto. Referring now to FIG. 5, one suitable demethanizer receives at least a portion of the light hydrocarbon product 117 for treatment in a cryogenic train 501, which includes one or more cold box heat exchangers 504, one or more refrigeration heat exchangers 505, and one or more vapor liquid separators 506. A vapor phase removed from vapor-liquid separators 506 is fractionated in splitter 502 and removed as a tail gas 503. The tail gas typically comprises methane and molecular hydrogen, and can be utilized as a fuel, e.g., for burners located in the steam cracking furnace. A liquid phase from vapor-liquid separators 506 is fractionated in splitter 502 and removed as a $C_{2+}$ product via line 507. Additional pretreatment stages 508 can be used, e.g., for removing from the $C_{2+}$ product at least a portion of one or more of, ammonia, carbon dioxide, arsine, mercury, hydrogen sulfide, carbonyl sulfide, mercaptans, and carbon disulfide, oxygenates and water. Stage 508 can be located downstream of splitter 502 as shown, upstream of cryogenic train 501, or at both locations—with some contaminants removed at the upstream location and others removed at the downstream location. The pretreated light hydrocarbon product is conducted to stage 165 via line 305.

Referring now to FIG. 6, another suitable demethanizer receives at least a portion of the light hydrocarbon product 117, which is conducted into absorber 601. A lean absorbent comprising $C_4$ hydrocarbon and/or $C_3$ hydrocarbon is conducted via line 608 and line 602 to absorber 601 via reflux drum 604. Typically the lean absorbent comprises $C_4$ hydrocarbon, e.g., $C_4$ hydrocarbon from line 309 of FIG. 3. The absorbent contacts the light hydrocarbon product in countercurrent flow, and rich absorbent is conducted away from absorber 601 via line 606. The tail gas comprising molecular hydrogen and methane is conducted away from absorber 601 via line 603 to reflux drum 604, and away via line 605. Rich absorbent is introduced into lean oil column 607 for separation and recovery of lean absorbent 608. The $C_{2+}$ product is conducted away via line 610 to optional stage 508, which serves the same purpose and can be utilized in the same locations as indicated in the discussion of the aspects illustrated by FIG. 5. Likewise, the pretreated light hydrocarbon product is conducted to stage 165 via line 305.

Those skilled in the art will appreciate that $C_4$ hydrocarbon 309 can be recovered in one or more debutanizers located in stage 165. The $C_4$ hydrocarbon 309 typically comprises normal and iso butanes, normal and iso butenes, and butadiene. The $C_4$ hydrocarbon 309 may further comprise contaminants such as acidic gases. The $C_4$ hydrocarbon 309 can be treated (e.g., by caustic and/or amine contacting) to make a purified $C_4$ hydrocarbon stream. Typically butadiene is separated from the $C_4$ hydrocarbon (and/or purified $C_4$ hydrocarbon), e.g., by extractive distillation) to produce a $C_4$ raffinate. The raffinate can be further processed in an optional contaminant removal stage to produce a purified raffinate. The raffinate and/or purified raffinate is typically processed in a selective hydroprocessing stage to convert at least a portion of the butadiene to mainly butenes instead of butanes. The hydroprocessed raffinate, typically comprises normal and iso butanes, and normal and iso butenes. Isobutene can be separated from the hydroprocessed raffinate by selective isobutene conversion to oxygenate such as MTBE and/or alkylate such as isooctene, with the conversion product(s) being recovered as a liquid phase from the primarily vapor-phase normal butane, isobutane, and normal butenes. Isobutene can be recovered from MTBE by a catalytic decomposition which typically produces isobutene, methanol, and water. Alternatively and/or in addition, alkylate and/or oxygenates (MTBE, MSBE, methanol, etc.) can be conducted away, e.g., for sale as a motor gasoline blendstock. It is observed that a $C_4$ hydrocarbon stream produced by steam cracking is richer in butadiene than a $C_4$ stream produced by FCC. For example, in certain aspects, the $C_4$ hydrocarbon in the effluent of steam cracker 104 contains butadiene in an amount $A_1$ and the $C_4$ hydrocarbon in the effluent of FCC 112 contains butadiene in an amount $A_2$, where $A_1 > A2$, e.g., $A_1 \geq 1.1*A_2$, such as $A_1 \geq 1.5*A_2$, or $A_1 \geq 2*A_2$, or $A_1 \geq 5*A_2$, $A_1 \geq 10*A_2$, or $A_1 \geq 100*A_2$, or $A_1 \geq 1000*A_2$, or $A_1$ is in a range of from $1.5*A_2$ to $100*A_2$, or $2*A_2$ to $50*A_2$. It has surprisingly been found that this difference in observed butadiene amounts can be utilized to improve process efficiency. Certain aspects developed in accordance with this improvement are shown schematically in FIG. 4.

Figure 4:
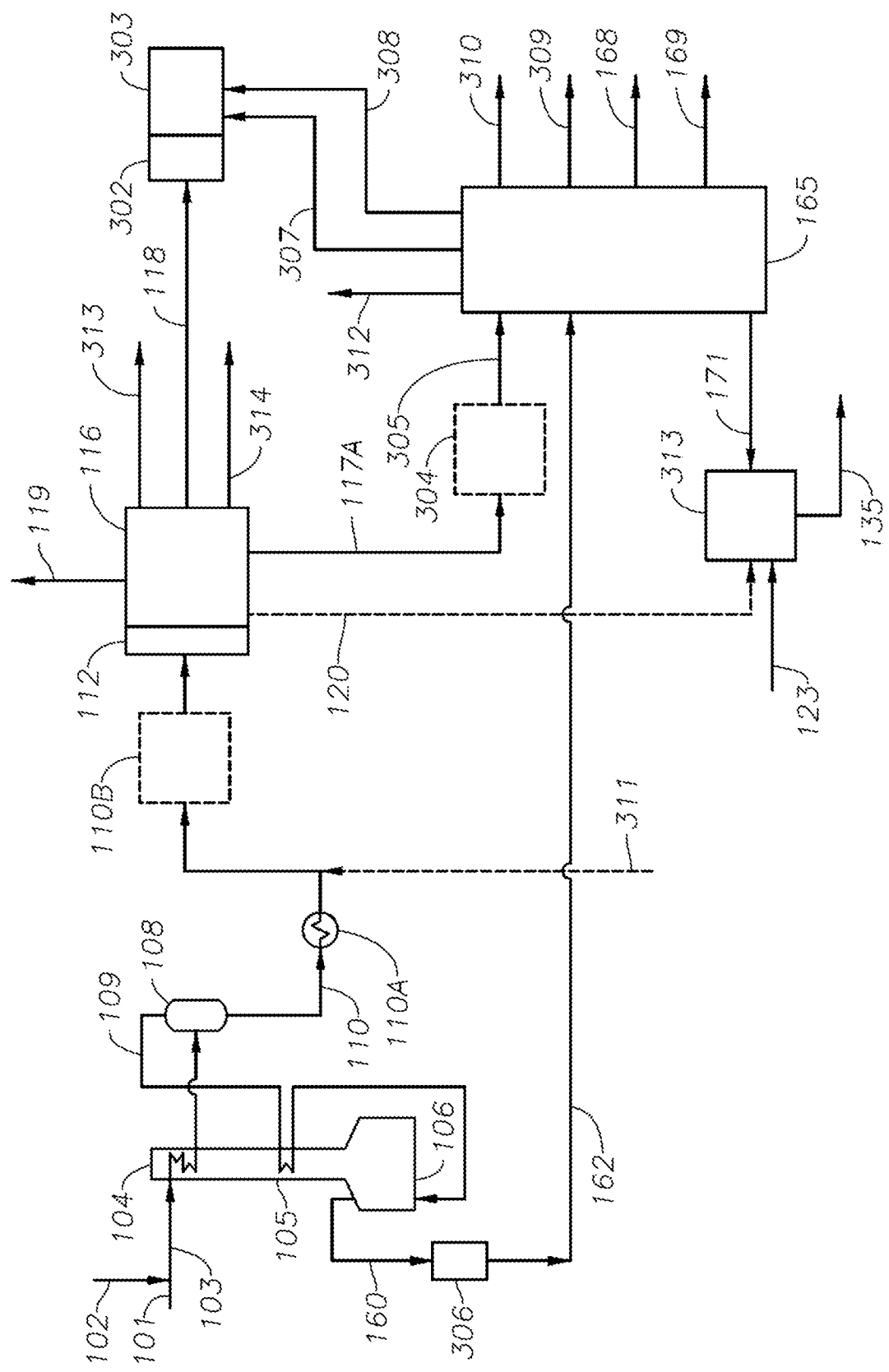
FIG. 4 schematically shows certain aspects which include separating from an FCC effluent a $C_4$ hydrocarbon stream that is lean in butadiene.

The aspects shown in FIG. 4 differ from those of FIG. 3 e.g., in that a $C_3$ hydrocarbon 313 and a $C_4$ hydrocarbon 314 are separated and recovered in second separator 116 from the effluent of FCC 112, in addition to $C_3$ hydrocarbon 310 and $C_4$ hydrocarbon 309 that are recovered from the steam cracker effluent in fifth separation stage 165. In other words, streams comprising $C_3$ hydrocarbon and $C_4$ hydrocarbon are withdrawn and removed from the effluent of FCC 112 such that the light hydrocarbon product of line 117A contains less $C_4$ hydrocarbon and less $C_3$ hydrocarbon than does the light hydrocarbon product of line 117 in FIG. 3. In certain aspects, the light hydrocarbon product comprises (i) ≤1 wt. % of $C_3$ hydrocarbon, e.g., ≤0.1 wt. %, such as ≤0.01 wt. %, or ≤0.001 wt. %; and/or (ii)≤1 wt. % of $C_4$ hydrocarbon, e.g., ≤0.1 wt. %, such as ≤0.01 wt. %, or ≤0.001 wt. %. For example, the light hydrocarbon product of line 117A can be substantially-free of $C_3$ hydrocarbon and substantially free of $C_4$ hydrocarbon. These aspects will now be described in more detail. The invention is not limited to these aspects, and this description is not meant to foreclose other aspects within the broader scope of the invention, such as those in which (i) the $C_3$ hydrocarbon in the FCC effluent is separated and recovered in stage 116 and (ii) the $C_4$ hydrocarbon in the FCC effluent is conducted away from 116 with the light hydrocarbon product 117A, and vice versa.

In certain aspects the separations of second separation stage 116 include separating a $C_{4+}$ hydrocarbon stream, $C_{3-}$ hydrocarbon stream, and a bottoms product from an FCC effluent. The bottoms product is conducted away via line 120 as shown in FIG. 4. A $C_4$ hydrocarbon stream and a $C_{5+}$ hydrocarbon are separated from the $C_{4+}$ hydrocarbon stream in one or more separators, typically located in stage 116. The $C_{5+}$ hydrocarbon is typically conducted away, e.g., for storage and/or further processing. A tail gas typically comprising molecular hydrogen, methane, nitrogen oxides, nitrogen, and carbon monoxide can be separated from the $C_{3-}$ hydrocarbon stream in one or more absorption demethanizers. The absorption demethanizer described in connection with FIG. 5 is suitable, but the invention is not limited thereto. Referring now to FIG. 5, the $C_{3-}$ hydrocarbon stream is introduced into absorber 601. The lean absorbent comprising $C_4$ hydrocarbon contacts the $C_{3-}$ hydrocarbon in countercurrent flow, and rich absorbent is conducted away from absorber 601 via line 606. Typically following an optional contaminant-removal stage, the $C_4$ hydrocarbon stream is combined (not shown in FIG. 6) with the rich absorbent of line 606. The combined stream is introduced into one or more lean oil columns 607 (typically one or more depropanizers) for separation and recovery of lean absorbent and a stream comprising $C_2$ hydrocarbon and $C_3$ hydrocarbon (the "$C_2/C_3$ stream"). A first portion of the lean absorbent, mainly comprising $C_4$ hydrocarbon, is conducted via line 608 and line 602 to absorber 601 via reflux drum 604. A second portion of the lean absorbent (not shown in FIG. 6) can be treated to remove acidic gases, and conducted away from stage 116 via line 314, as shown in FIG. 4. The second portion of the lean absorbent 314 can be introduced (not shown) into stage 165. Since the second portion of the lean absorbent 314 is a $C_4$ hydrocarbon stream that is lean in butadiene, at least a portion of the lean absorbent 314 can be added to the $C_4$ raffinate of stage 165 (e.g., downstream of the location where butadiene is removed from the $C_4$ hydrocarbon derived from the steam cracker effluent). The tail gas is conducted away from absorber 601 via line 603 to reflux drum 604, and away via line 605. A $C_2$ hydrocarbon stream and a $C_3$ hydrocarbon stream can be separated from the $C_2/C_3$ stream, e.g., for storage and/or further processing. These aspects are advantageous in that relatively pure $C_2$, $C_3$ and $C_4$ hydrocarbon streams can be separated and recovered within stage 116 by utilizing an absorption demethanation stage using as an absorbent a $C_4$ hydrocarbon stream separated from the FCC effluent in stage 116. In other words, the absorbent is produced internally, and is not obtained from a source external to stages 112 and 116. Although these aspects have been described as including one absorber and one lean oil tower (e.g., a depropanizer), those skilled in the art will appreciate that a plurality of absorbers and lean oil towers can be used.

In other aspects, the $C_{3-}$ hydrocarbon stream and the $C_{5+}$ hydrocarbon stream are introduced into an absorption deethanizer utilizing the $C_{5+}$ stream as the absorbent. The second portion of the lean absorbent, in these aspects mainly $C_{3+}$ hydrocarbon, is conducted away, e.g., for storage and/or further processing. Overhead from the deethanizer lean oil tower, comprising mainly $C_2$ hydrocarbon and $C_3$ hydrocarbon, is typically treated for acidic gas removal, and then processed for recovery of a $C_3$ hydrocarbon stream (typically conducted away for use as a $C_3$ refrigerant), and a $C_4$ hydrocarbon stream 314 that is lean in butadiene. The $C_4$ hydrocarbon steam can be combines with the $C_4$ raffinate of stage 165, as described in connection with the preceding aspects. Overhead from the deethanizer reflux drum can be treated for contaminant removal, and then conducted to one or more absorption demethanizer (as previously described) for recovery of the tail gas stream and a $C_2$ hydrocarbon stream.

In certain aspects shown in FIGS. 3 and 4, the hydrocarbon feed 101 is a portion of hydrocarbon obtained from a hydrocarbon source, e.g., a crude oil source. In these and other aspects, a second portion of the hydrocarbon source can be conducted to at least one atmospheric distillation zone and/or at least one vacuum distillation zone—these zones. At least one vacuum distillation zone is typically located downstream of an atmospheric distillation zone, with atmospheric distillation zone bottoms feeding the vacuum distillation zone for additional distillation, but this is not required. Optionally, atmospheric distillation bottoms and/or vacuum distillation bottoms are conducted via line 311, e.g., for mixing with the first liquid phase product. Optionally, the bottoms product 120 is conducted to stage 313 for hydroprocessing with the tar product-diluent mixture 171. Cycle oil 119 can be utilized to flux the bottoms product, as described in connection with the aspects illustrated by FIGS. 1 and 2.

While the foregoing is directed to embodiments of the present invention, other and further embodiments of the invention may be devised without departing from the basic scope thereof, and the scope thereof is determined by the claims that follow.

What is claimed is:

1. A hydrocarbon upgrading process, comprising:
   heating a hydrocarbon feed and combining the hydrocarbon feed with an aqueous fluid to produce a heated mixture comprising hydrocarbon and steam, wherein the heating is carried out before, during, and/or after the hydrocarbon feed is combined with the aqueous fluid;
   separating, from the heated mixture, a vapor phase product and a liquid phase product;
   catalytically cracking at least a portion of the liquid phase product in the presence of a fluidized catalyst to produce a catalytically cracked effluent;
   separating a light hydrocarbon product and a bottoms product from the catalytically cracked effluent, wherein the light hydrocarbon product comprises a first $C_2$ hydrocarbon;
   steam cracking at least a portion of the vapor phase product to produce a steam cracker effluent;
   separating, from the steam cracker effluent, a tar product and an upgraded steam cracker effluent, wherein the upgraded steam cracker effluent comprises a second $C_2$ hydrocarbon;
   hydroprocessing at least a portion of the tar product with at least a portion of the bottoms product to produce a hydroprocessed product, the at least a portion of the bottoms product and the at least a portion of the tar product being combined before and/or during the hydroprocessing; and
   combining at least a portion of the first $C_2$ hydrocarbon and at least a portion of the second $C_2$ hydrocarbon, and recovering at least a portion of the combined $C_2$ hydrocarbon.

2. The process of claim 1, wherein
   (i) the hydroprocessing is carried out under the pre-treater hydroprocessing conditions to produce a pretreated tar product;
   (ii) the pre-treater hydroprocessing conditions include hydroprocessing the tar product at a temperature ($T_{PT}$) of 400° C. or less, a weight hour space velocity (WHSV$_{PT}$) of ≥0.3 hr$^{-1}$ based on a weight of the tar product that is subjected to the pre-treater hydroprocessing conditions, a total pressure ($P_{PT}$) of ≥6 MPa, and in the presence of molecular hydrogen supplied at a rate (SR$_{PT}$) of less than 534 standard cubic meters per cubic meter of the tar product that is subjected to the pre-treater hydroprocessing conditions,
   (iii) the pre-treated tar product comprises a vapor potion and a liquid portion;
   (iv) the hydroprocessed product is obtained by hydroprocessing the pre-treated tar product under bottoms product hydroprocessing conditions which include hydroprocessing the pre-treated tar product at a temperature ($T_{BP}$) of ≥200° C., a weight hour space velocity (WHSV$_{BP}$) of ≥0.3 hr$^{-1}$ based on a weight of the pre-treated tar product, a total pressure ($P_{BP}$) of ≥6 MPa, and in the presence of molecular hydrogen supplied at a rate (SR$_{BP}$) of ≥534 standard cubic meters per cubic meter of the pre-treated tar product; and
   (v) WHSV$_{BP}$ is less than WHSV$_{PT}$.

3. The process of claim 1, further comprising (i) pretreating the liquid phase product upstream of the catalytic cracking, and (ii) heating or cooling the liquid phase product upstream and/or downstream of the pretreating, wherein the pretreating includes one or more of desalting, hydroprocessing, and particulate removal.

4. The process of claim 1, further comprising pretreating the light hydrocarbon product before combining the first and second $C_2$ hydrocarbons, wherein the pretreating includes removing from the light hydrocarbon product at least a portion of one or more of molecular hydrogen, methane, ammonia, carbon dioxide, arsine, mercury, hydrogen sulfide, carbonyl sulfide, mercaptans, and carbon disulfide, oxygenates and water.

5. The process of claim 1, wherein (i) the light hydrocarbon product further comprises a first $C_3$ hydrocarbon; (ii) the upgraded steam cracker effluent further comprises a second $C_3$ hydrocarbon; (iii) the process further comprises combining at least a portion of the first $C_3$ hydrocarbon and at least a portion of the second $C_3$ hydrocarbon, and recovering at least a portion of the combined $C_3$ hydrocarbon; and wherein the process further comprises one or more of (a) comprises recovering propylene from at least a portion of one or more of the first $C_3$ hydrocarbon, the second $C_3$ hydrocarbon, and the combined $C_3$ hydrocarbon, and (b) recovering ethylene from at least a portion of one or more of the first $C_2$ hydrocarbon, the second $C_2$ hydrocarbon, and the combined $C_2$ hydrocarbon.

6. The process of claim 1, further comprising:
   separating a naphtha from the catalytically cracked effluent;
   hydroprocessing at least a portion of the naphtha to produce a hydroprocessed naphtha;
   reforming the hydroprocessed naphtha to produce a reformate and molecular hydrogen; and
   utilizing at least a portion of the molecular hydrogen for at least one of the tar product hydroprocessing and the naphtha hydroprocessing.

7. The process of claim 1, wherein the hydrocarbon feed comprises medium hydrocarbon and/or heavy hydrocarbon.

8. The process of claim 1, further comprising (i) providing a crude oil, wherein the hydrocarbon feed comprises a first portion of the crude oil, (ii) distilling at least a second portion of the crude oil in at least one atmospheric distillation zone and/or at least one vacuum distillation zone, (iii) conducting an atmospheric bottoms product away from the atmospheric distillation zone, (iv) conducting a vacuum bottoms product away from the vacuum distillation zone, and (v) combining with the liquid phase product at least a portion of the atmospheric bottoms product and/or the vacuum bottoms product.

9. The process of claim 1, wherein the upgraded steam cracker effluent further comprises benzene and/or toluene, and wherein the process further comprises (i) recovering at least a portion of the toluene and/or at least a portion of the benzene and (ii) combining with the reformate at least a portion of the recovered benzene and/or at least a portion of the recovered toluene.

10. The process of claim 1, wherein the upgraded steam cracker effluent further comprises benzene and/or toluene, and wherein the process further comprises (i) recovering at least a portion of the toluene and/or at least a portion of the benzene, and (ii) alkylating a portion of the recovered benzene and/or at least a portion of the recovered toluene to produce one or more of additional toluene, ethylbenzene, and xylene.

11. A hydrocarbon upgrading process, comprising:
heating a hydrocarbon feed and combining the hydrocarbon feed with an aqueous fluid to produce a heated mixture comprising hydrocarbon and steam, wherein the heating is carried out before, during, and/or after the hydrocarbon feed is combined with the aqueous fluid;
separating from the heated mixture a vapor phase product and a liquid phase product;
catalytically cracking the liquid phase product in the presence of a fluidized catalyst to produce a catalytically cracked effluent;
separating a light hydrocarbon product and a bottoms product from the catalytically cracked effluent, wherein the light hydrocarbon product comprises methane, a first $C_2$ hydrocarbon, a first $C_3$ hydrocarbon, and a first $C_4$ hydrocarbon;
separating, from the light hydrocarbon product, at least a portion of the first $C_4$ hydrocarbon to produce an upgraded light hydrocarbon product;
demethanizing at least a portion of the upgraded light hydrocarbon product by at least contacting that portion of the upgraded light hydrocarbon product with a first portion of the first $C_4$ hydrocarbon, and recovering (i) a raffinate comprising methane and (ii) an extract comprising $C_2$, $C_3$, and $C_4$ hydrocarbon;
steam cracking the vapor phase product to produce a steam cracker effluent;
separating from the steam cracker effluent a tar product and an upgraded steam cracker effluent, wherein the upgraded steam cracker effluent comprises a second $C_2$ hydrocarbon; a second $C_3$ hydrocarbon, and a second $C_4$ hydrocarbon, wherein the second $C_4$ hydrocarbon is richer in butadiene in comparison with the first $C_4$ hydrocarbon;
hydroprocessing at least a portion of the tar product with at least a portion of the bottoms product to produce a hydroprocessed product, the at least a portion of the bottoms product and the at least a portion of the tar product being combined before and/or during the hydroprocessing;
removing butadiene from the second $C_4$ hydrocarbon to produce an upgraded $C_4$ hydrocarbon; and
combining at least a portion of the extracted $C_4$ hydrocarbon with at least a portion of the upgraded $C_4$ hydrocarbon.

12. The process of claim 11, further comprising recovering ethylene from at least a portion of the extracted $C_2$ hydrocarbon and/or a portion of the second $C_2$ hydrocarbon.

13. The process of claim 11, further comprising pretreating the light hydrocarbon product before combining the first and second $C_2$ hydrocarbons, wherein the pretreating includes removing from the light hydrocarbon product at least a portion of one or more of molecular hydrogen, methane, ammonia, carbon dioxide, arsine, mercury, hydrogen sulfide, carbonyl sulfide, mercaptans, and carbon disulfide, oxygenates and water.

14. The process of claim 11, further comprising (i) combining at least a portion of the extracted $C_2$ hydrocarbon and at least a portion of the second $C_2$ hydrocarbon, (ii) recovering at least a portion of the combined $C_2$ hydrocarbon, and (iii) recovering ethylene from at least a portion of the combined $C_2$ hydrocarbon.

15. The process claim 11, wherein the process further comprises (i) combining at least a portion of the extracted $C_3$ hydrocarbon and at least a portion of the second $C_3$ hydrocarbon, and recovering at least a portion of the combined $C_3$ hydrocarbon; and/or (ii) comprises recovering propylene from at least a portion of one or more of the extracted $C_3$ hydrocarbon, the second $C_3$ hydrocarbon, and combined $C_3$ hydrocarbon.

16. The process claim 11, further comprising:
separating a naphtha from the catalytically cracked effluent;
hydroprocessing at least a portion of the naphtha to produce a hydroprocessed naphtha;
reforming the hydroprocessed naphtha to produce a reformate and molecular hydrogen; and
utilizing at least a portion of the molecular hydrogen for at least one of the tar product hydroprocessing and the naphtha hydroprocessing.

17. The process of claim 11, wherein the hydrocarbon feed comprises medium hydrocarbon and/or heavy hydrocarbon.

18. The process of claim 11, further comprising (i) providing a crude oil, wherein the hydrocarbon feed comprises a first portion of the crude oil, (ii) distilling at least a second portion of the crude oil in at least one atmospheric distillation zone and/or at least one vacuum distillation zone, (iii) conducting an atmospheric bottoms product away from the atmospheric distillation zone, (iv) conducting a vacuum bottoms product away from the vacuum distillation zone, and (v) combining with the liquid phase product at least a portion of the atmospheric bottoms product and/or at least a portion of the vacuum bottoms product.

19. The process of claim 11, wherein the upgraded steam cracker effluent further comprises benzene and/or toluene, and wherein the process further comprises (i) recovering at least a portion of the toluene and/or at least a portion of the benzene and (ii) combining with the reformate at least a portion of the recovered benzene and/or at least a portion of the recovered toluene.

20. The process of claim 11, wherein the upgraded steam cracker effluent further comprises benzene and/or toluene, and wherein the process further comprises (i) recovering at least a portion of the toluene and/or at least a portion of the benzene, and (ii) alkylating a portion of the recovered benzene and/or at least a portion of the recovered toluene to produce one or more of additional toluene, ethylbenzene, and xylene.

* * * * *